US010203269B2

(12) United States Patent
Eriksen et al.

(10) Patent No.: US 10,203,269 B2
(45) Date of Patent: *Feb. 12, 2019

(54) METHOD OF RETRIEVING ELEMENTS FROM FIXED TISSUE

(71) Applicant: University of Houston System, Houston, TX (US)

(72) Inventors: Jason Eriksen, Houston, TX (US); Craig Vollert, Houston, TX (US); Steven Bark, Houston, TX (US); Wilna Moree, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,327

(22) Filed: Oct. 27, 2016

(65) Prior Publication Data
US 2017/0184476 A1 Jun. 29, 2017

Related U.S. Application Data

(63) Continuation-in-part of application No. 14/530,142, filed on Oct. 31, 2014, now Pat. No. 9,506,928.

(60) Provisional application No. 62/037,905, filed on Aug. 15, 2014, provisional application No. 61/915,271, filed on Dec. 12, 2013.

(51) Int. Cl.
*G01N 33/68* (2006.01)
*G01N 1/30* (2006.01)
*G01N 1/44* (2006.01)

(52) U.S. Cl.
CPC ............... *G01N 1/30* (2013.01); *G01N 1/44* (2013.01); *G01N 33/6803* (2013.01); *G01N 33/6878* (2013.01); *G01N 2001/305* (2013.01)

(58) Field of Classification Search
IPC ...................................................... G01N 1/30
See application file for complete search history.

(56) References Cited

U.S. PATENT DOCUMENTS

| 5,578,452 A | 11/1996 | Shi et al. |
| 6,960,450 B2 | 11/2005 | Namimatsu |
| 9,506,928 B2* | 11/2016 | Eriksen .............. G01N 33/6803 |
| 2007/0207505 A1 | 9/2007 | Kojima |
| 2009/0202998 A1 | 8/2009 | Schlumpberger et al. |
| 2010/0081606 A1 | 4/2010 | Barger et al. |
| 2012/0295279 A1 | 11/2012 | Kasamatsu |

FOREIGN PATENT DOCUMENTS

| CN | 10259774 A | 7/2012 |
| EP | 1376096 B1 | 10/2008 |
| WO | WO-0223156 A1 | 3/2002 |
| WO | WO-2008095501 A1 | 8/2008 |
| WO | WO-2011020612 A1 | 2/2011 |
| WO | WO-2011025442 A1 | 3/2011 |
| WO | WO-2013078650 A1 | 6/2013 |
| WO | WO 2015/088667 | 6/2015 |

OTHER PUBLICATIONS

Shigeki N. Reversing the Effects of Formalin Fixation . . . The J of Histochemistry and Cytochemistry. 53(1)3-11, Jan. 2005. (Year: 2005).*
Vollert, C. et al. Formaldehyde Scavengers Function as Novel Antigen Retrieval Agents. Scientific Reports 5:17322, Nov. 27, 2015. (Year: 2015).*
Fowler C. et al. Modeling Formalin Fixation and Histological Processing with Ribonuclease A. Laboratory Invetigation 88(7)785-791, May 2008. (Year: 2008).*
Baschong W. et al. "Control of Autofluorescence of Archival Formaldehyde—fixed, Paraffin-embedded Tissue in Confocal Laser Scanning Microscopy (CLSM)", The Journal of Histochemistry & Cytochemistry, 2001, vol. 49(12), pp. 1565-1571.
Shi Shan-Rong et al. "Protein Extraction from Formalin-fixed, Paraffinembedded Tissue Sections: Quality Evaluation by Mass Spectrometry", Journal of Histochemistry & Cytochemistry, 2006, vol. 54(6), pp. 739-743.
Vollert, et all.; "Formaldehyde scavengers function as novel antigen retrieval agents"; Scientific Reports, vol. 5, Nov. 27, 2015, p. 17322.
Shi Shan-Rong et al. "Antigen retrieval immunohistochemistry under the influence of pH using monoclonal antibodies," Journal of Histochemistry & Cytochemistry, vol. 43, No. 2, Feb. 1, 1995, p. 193-201.
Bird et al; "Formaldehyde scavenging from peritoneal dialysis solutions using reduced aminothiol compounds," Nephrology, vol. 9, No. 2, Apr. 1, 2004, p. 65-72.

* cited by examiner

Primary Examiner — Ralph J Gitomer
(74) Attorney, Agent, or Firm — Winstead PC

(57) ABSTRACT

In some embodiments, the present disclosure pertains to a method for retrieving at least one molecular recognition element in a fixed tissue. In some embodiments the method comprises preparing a solution comprising at least one aldehyde-scavenging agent. In some embodiments, the method comprises contacting the fixed tissue with the solution. In some embodiments, the tissue is fixed with an aldehyde-based cross-linking agent. In some embodiments, a reaction of the aldehyde-scavenging agent with the aldehydes comprising the cross-linking agent retrieves the at least one molecular recognition element. In some embodiments, the at least one molecular recognition element comprises of amino acids, peptides, proteins, nucleic acids, carbohydrates, lipids, or a combination thereof. In some embodiments, the at least one aldehyde-scavenging agent comprises of beta-dicarbonyl compounds, mono or di-amide scavengers, ethyl alcohols, sulfur containing compounds, mercaptoethylamines, mercaptoethanols, hydrazines, ethanolamines, hydroxylamines, anilines, variation of amines, activated charcoal, phenols, or mixtures and combinations thereof.

27 Claims, 30 Drawing Sheets

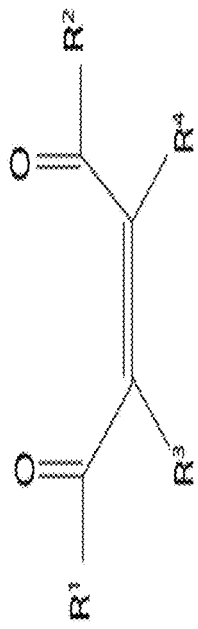
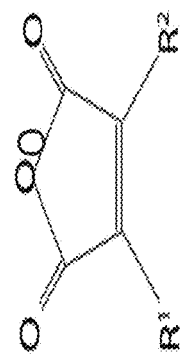
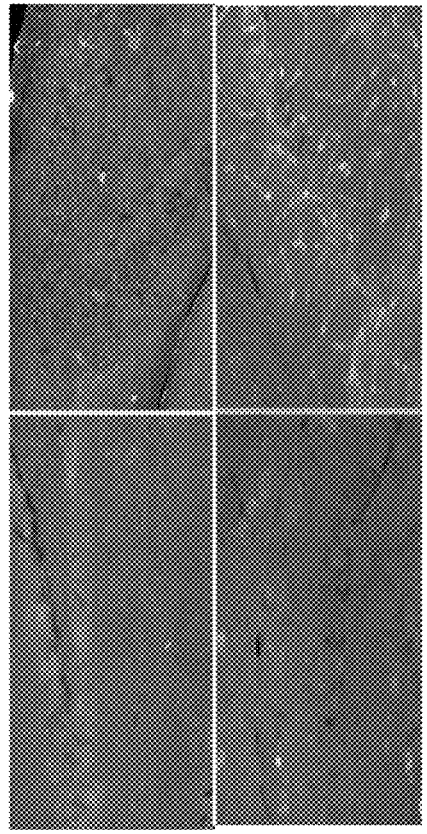
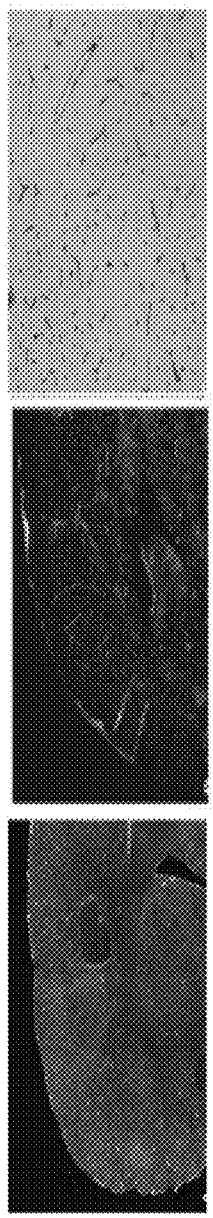
FIG. 1A
FIG. 1B
FIG. 2A
FIG. 2B
FIG. 2C
FIG. 2D
FIG. 3A
FIG. 3B
FIG. 3C

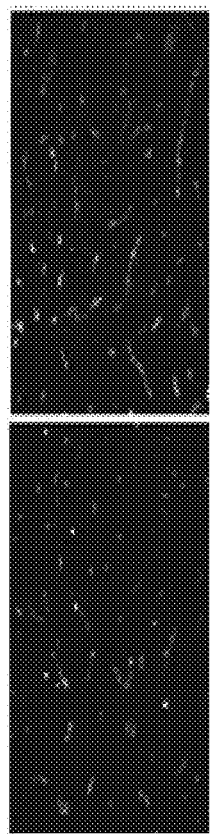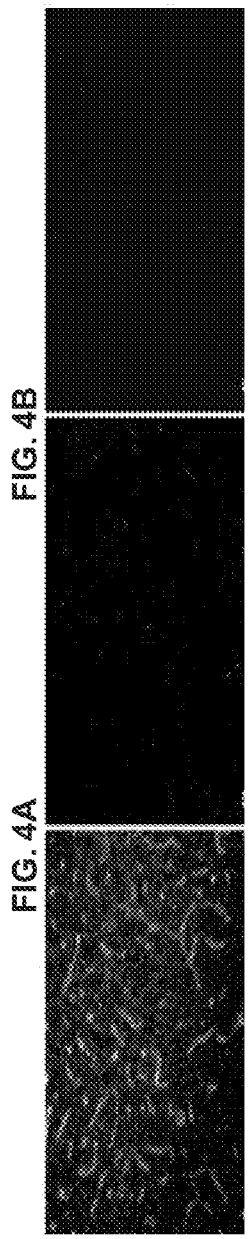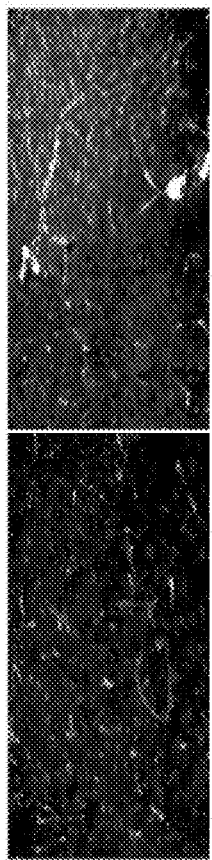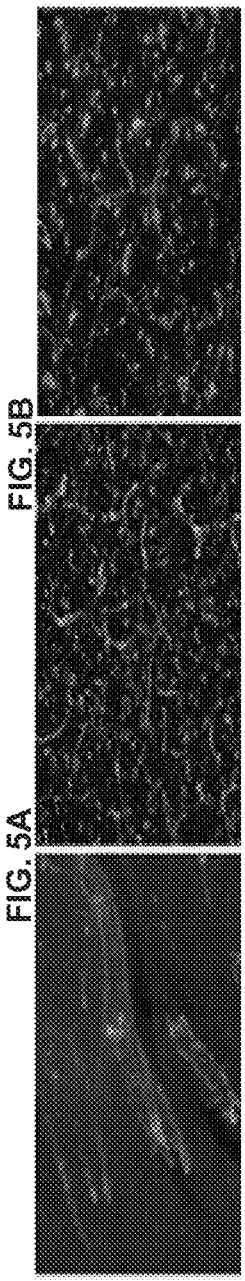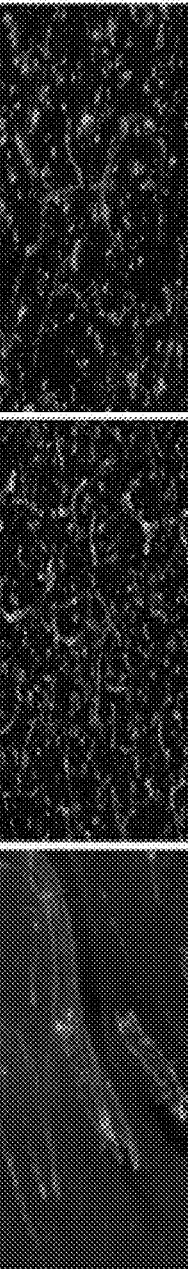

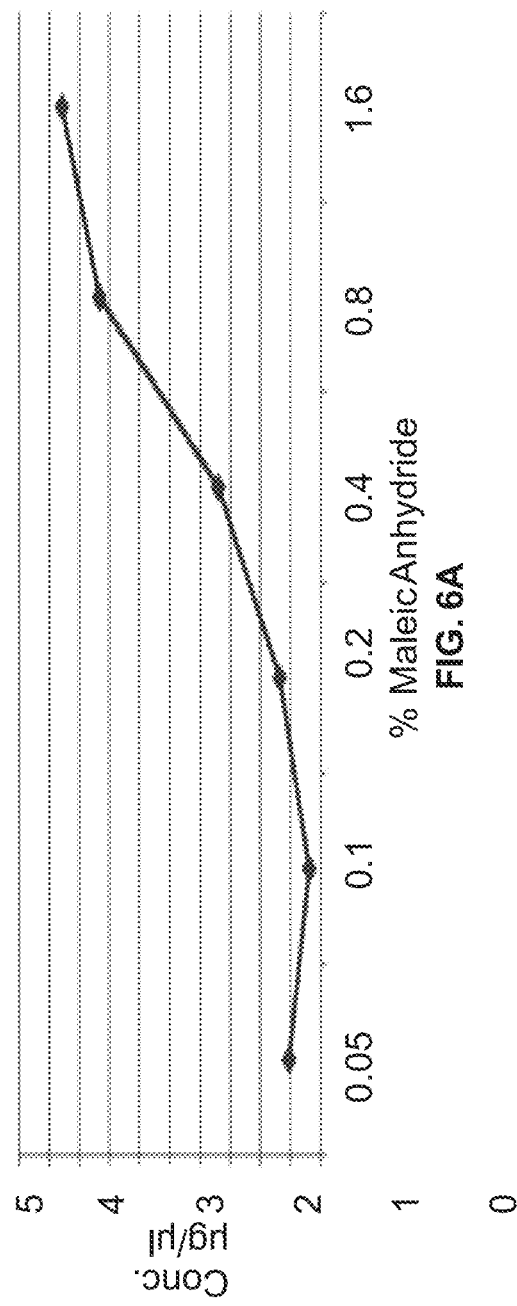
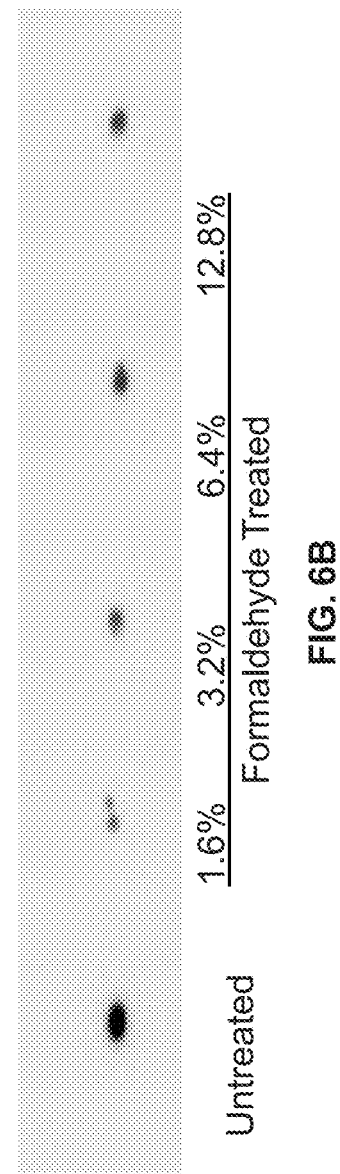
FIG. 6A
FIG. 6B

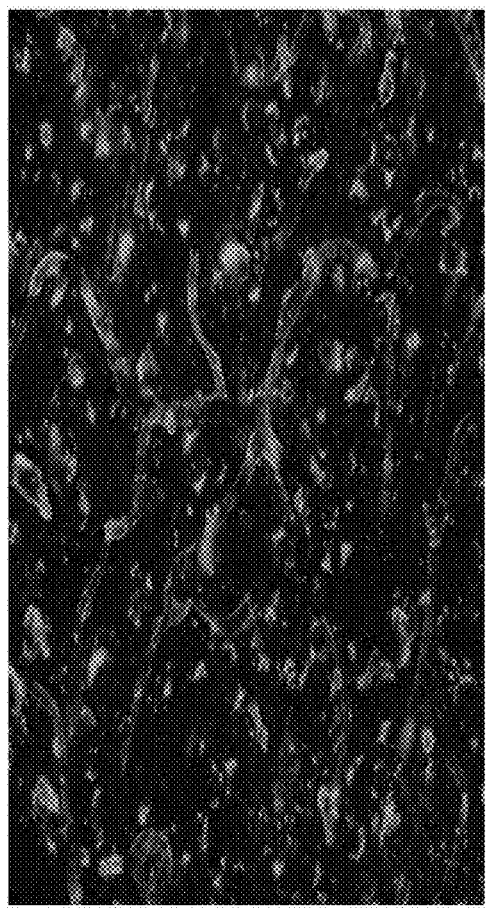
FIG. 7
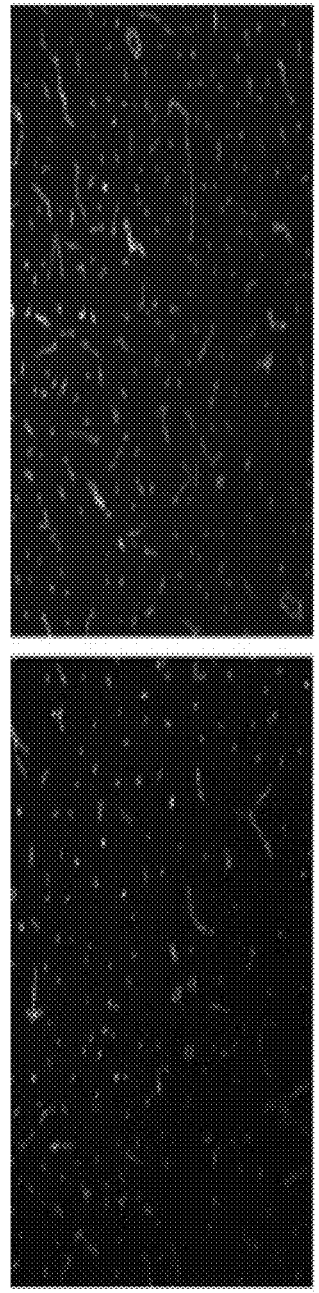
FIG. 8B
FIG. 8A

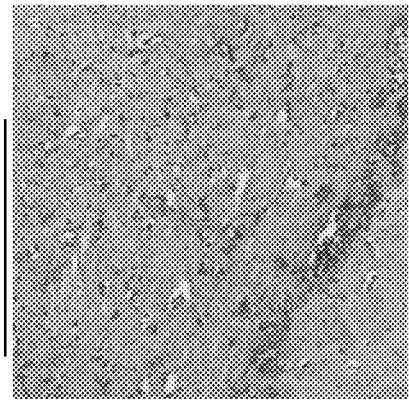
Fig. 14A 2-Pyrrolidinone
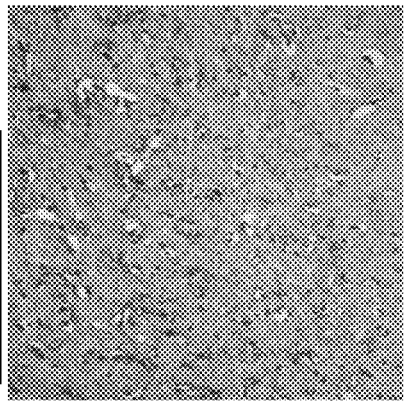
Fig. 14B Barbituric acid
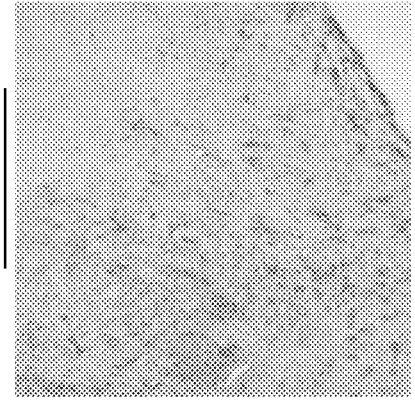
Fig. 14E Tannic acid
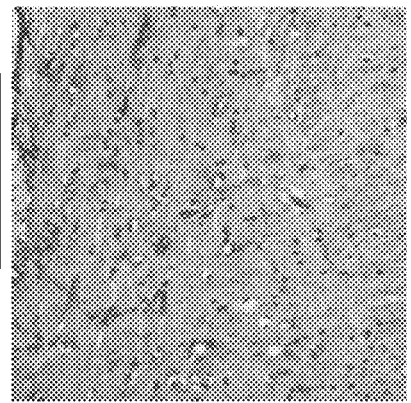
Fig. 14D Succinimide
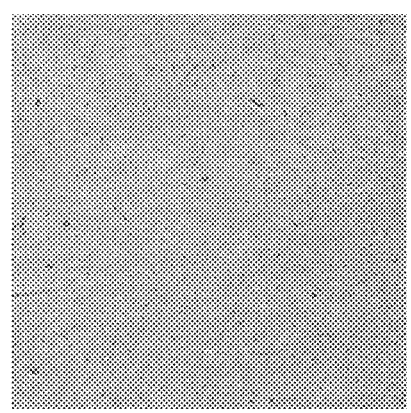
Fig. 14C L-Asparagine

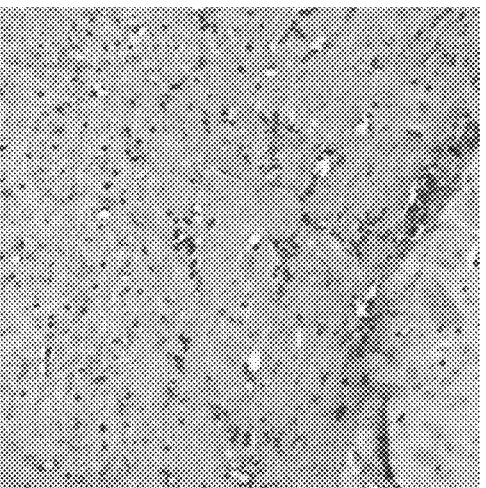
Fig. 16A 1,3,5-Triazine-2,4,6-Trithiol
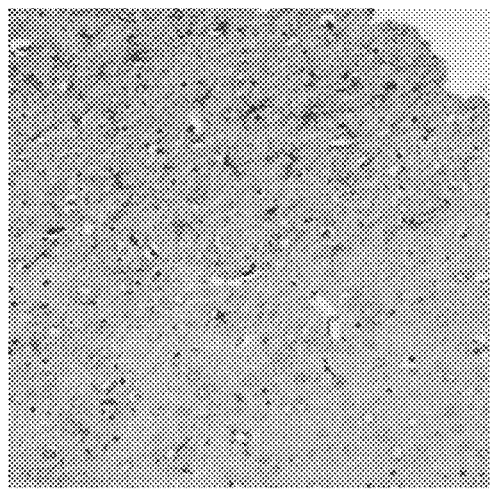
Fig. 16B Sodium bisulfite
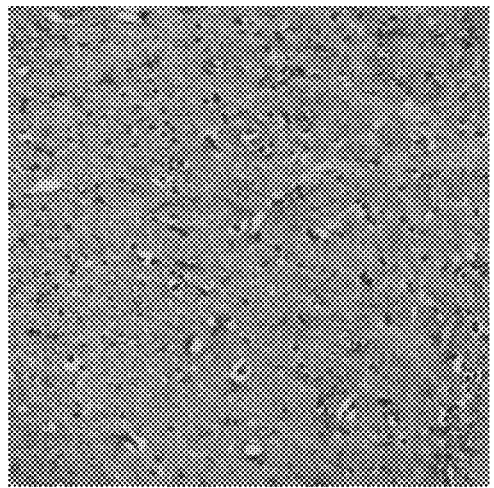
Fig. 16C Sodium metabisulfite O-Ethylhydroxlamine O-Benzylhydroxylamine O-(Carboxymethyl)hydroxylamine Hydroxylamine

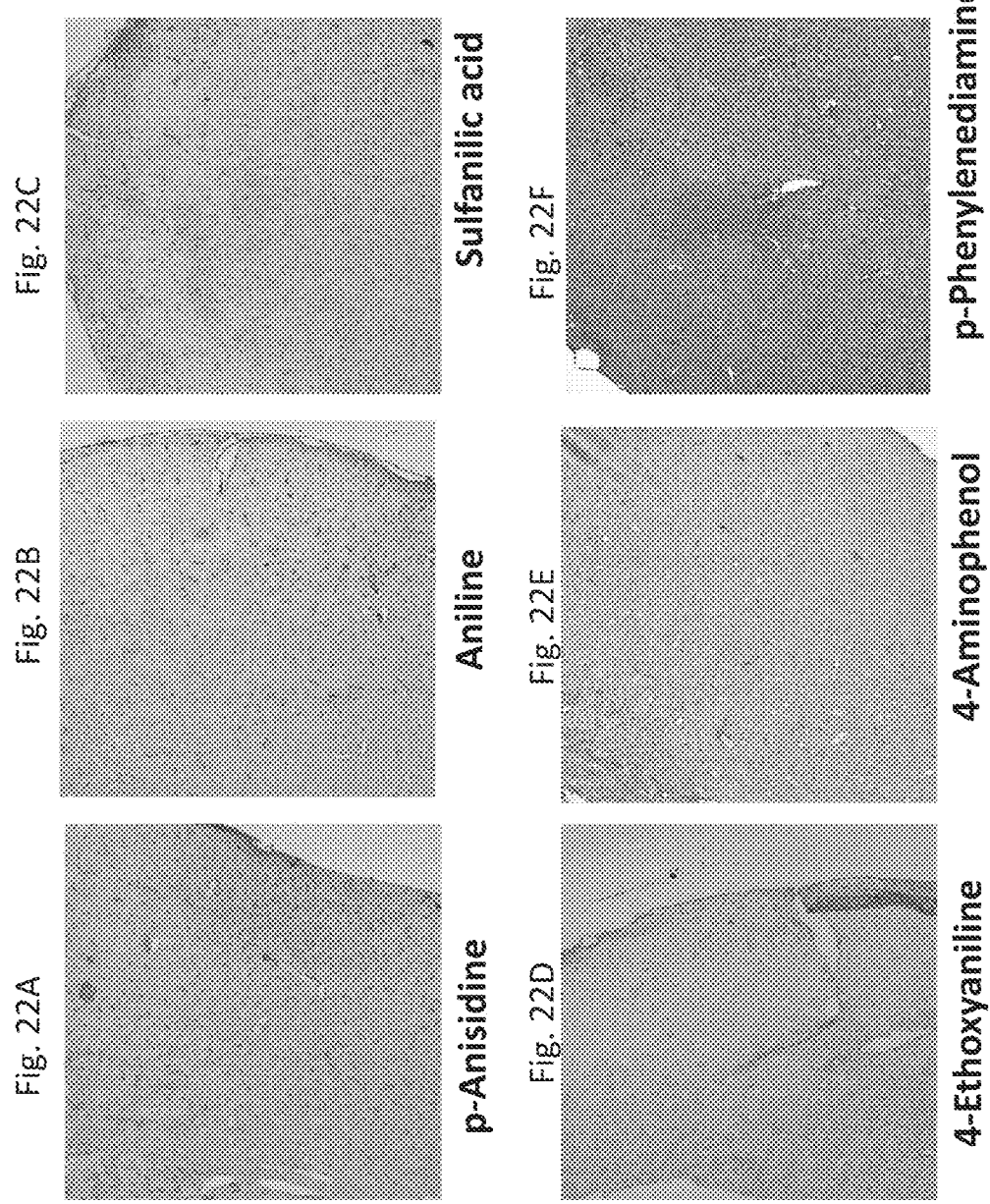

Pyridoxamine

Ammonium Bicarbonate

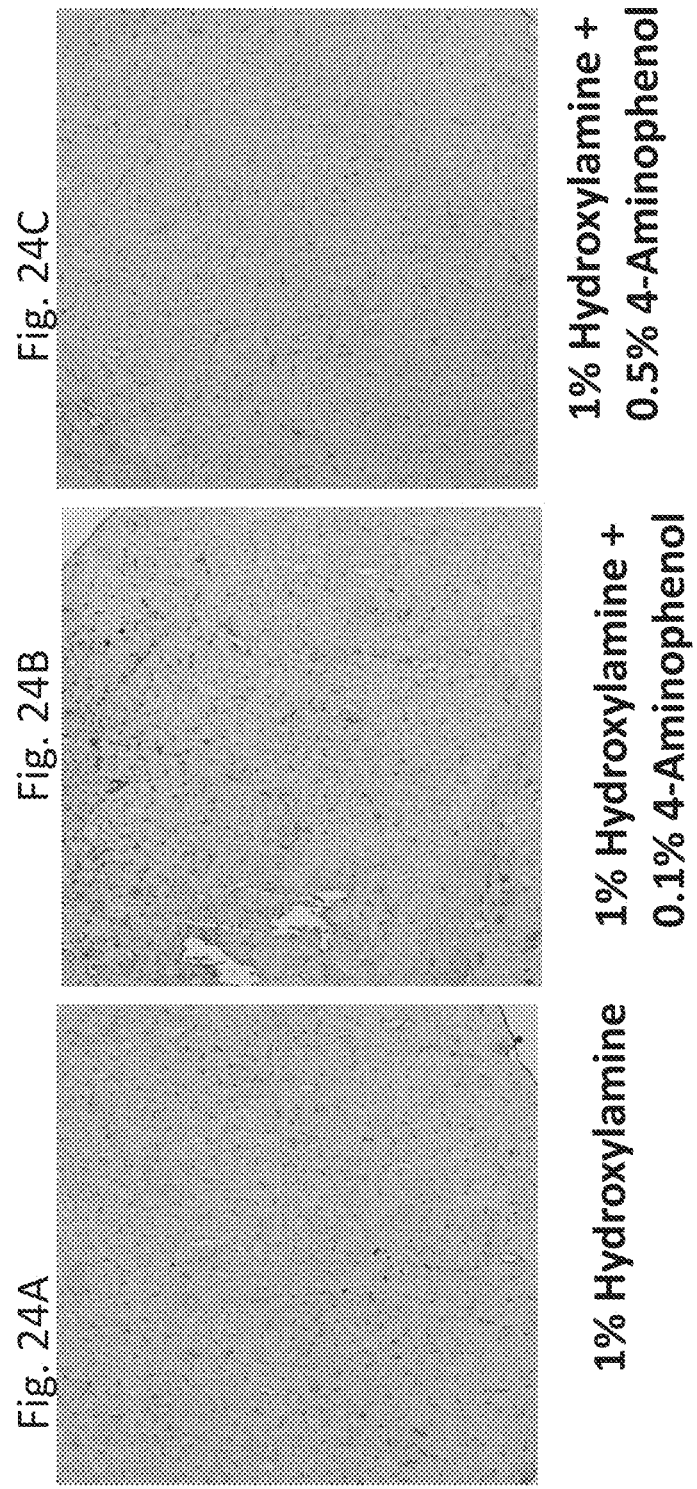

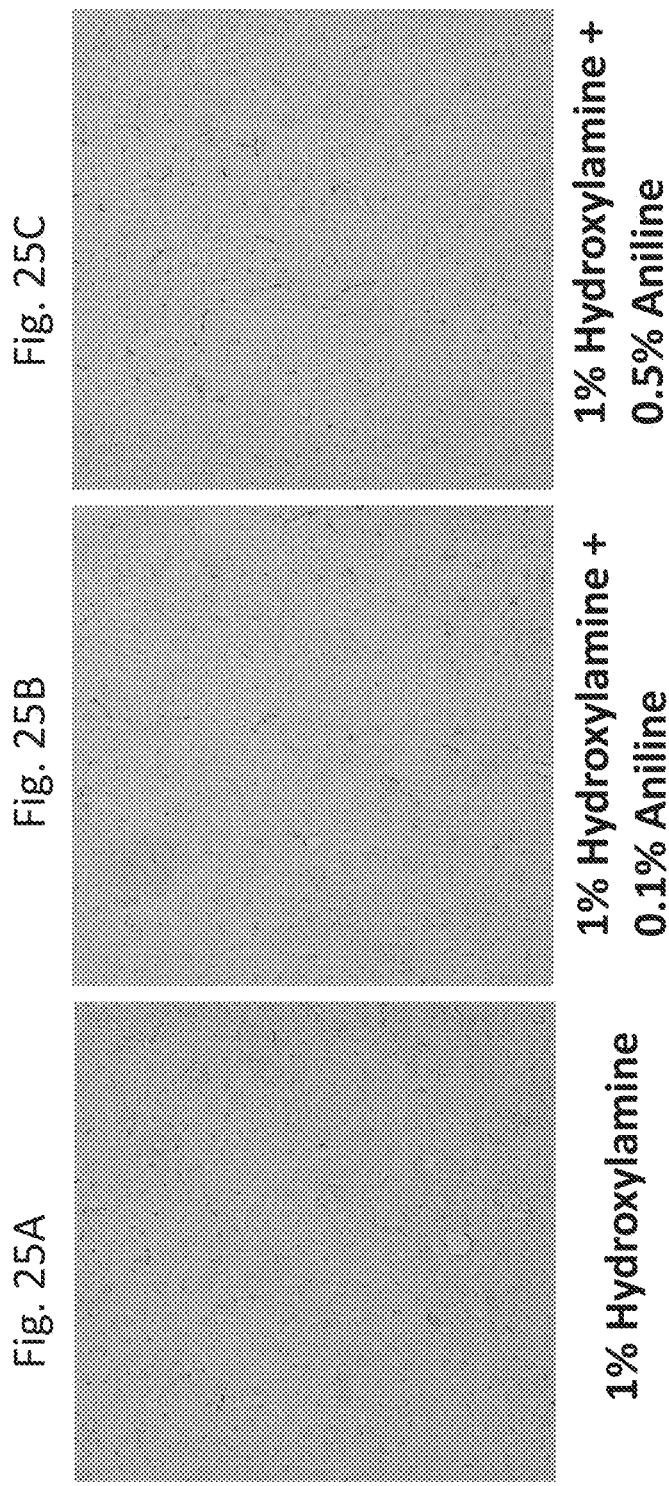

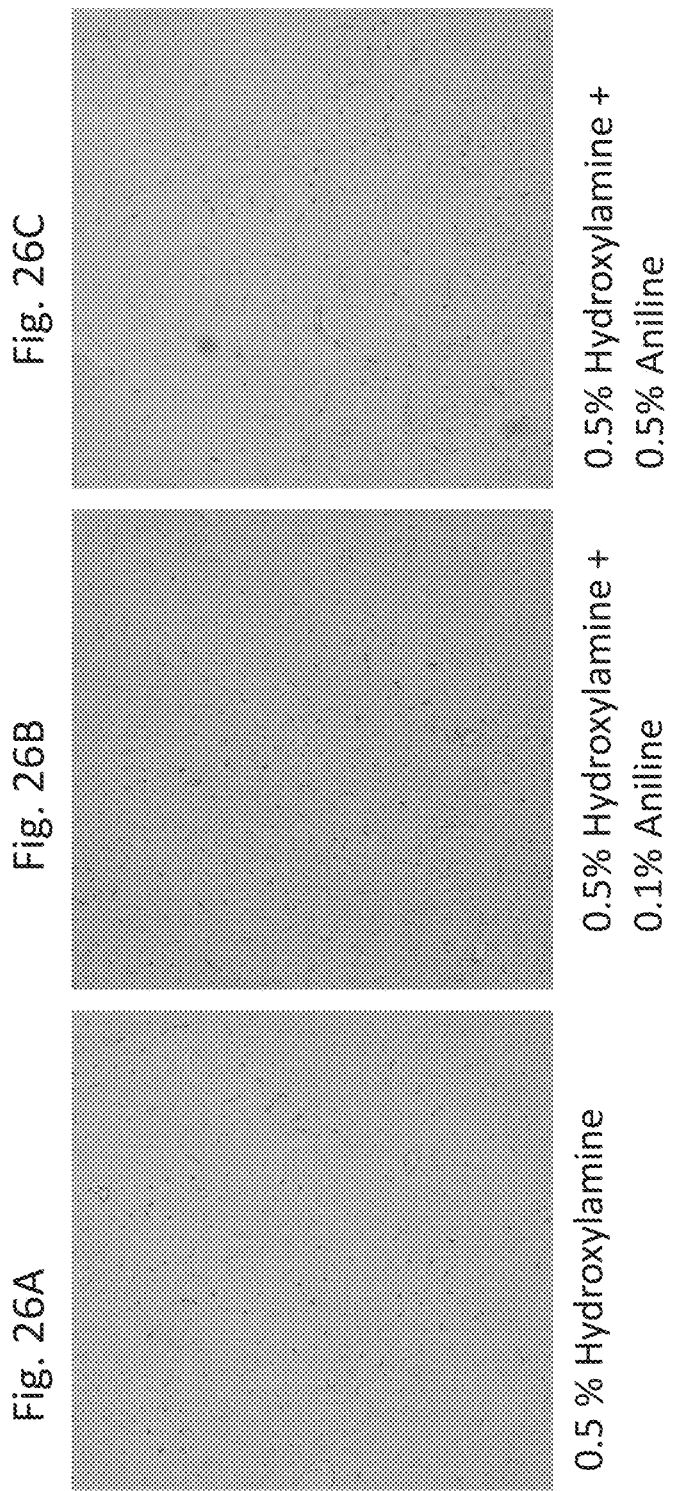

1% O-Benzylhydroxylamine

1% O-Benzylhydroxylamine
0.1% Aniline

1% O-Benzylhydroxylamine
0.5% Aniline 0.5% O-Benzylhydroxylamine 0.5% O-Benzylhydroxylamine + 0.1% Aniline 0.5% O-Benzylhydroxylamine + 0.5% Aniline

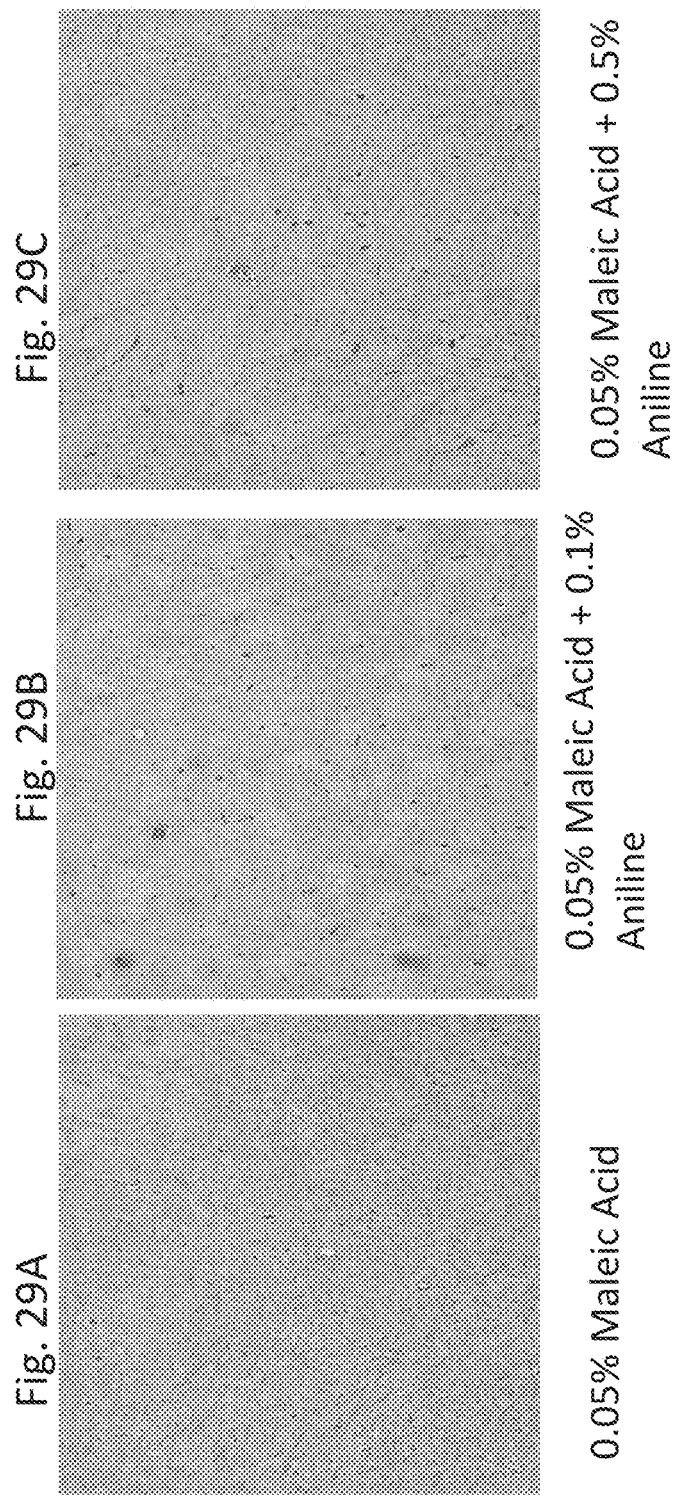

METHOD OF RETRIEVING ELEMENTS FROM FIXED TISSUE

CROSS-REFERENCE TO RELATED APPLICATIONS

This application is a continuation in part of and claims benefit of priority under § 35 U.S.C. § 120 of nonprovisional application U.S. Ser. No. 14/530,142, which in turn claims benefit of priority under 35 U.S.C. § 119(e) of provisional application U.S. Ser. No. 62/037,905, filed Aug. 15, 2014, and provisional application U.S. Ser. No. 61/915,271, filed Dec. 12, 2013, the entireties of both of which are hereby incorporated by reference.

FIELD OF THE INVENTION

The present invention relates generally to the fields of histology and the detection of molecular recognition elements, epitopes, or antigens of interest in compositions or tissues that have been preserved using an aldehyde-based cross-linking agent. Specifically, the present invention provides a method of activating, unmasking, or retrieving a molecular recognition element, an antigen, or an epitope that has been chemically modified by aldehyde fixatives contained in the compositions or tissues, using aldehyde-scavenging agents.

BACKGROUND

The nature of tissue processing requires that the samples be "fixed" prior to embedding in paraffin and micro-sectioning on a microtome to produce tissue sections suitable for immunostaining. The vast majority of fixation procedures, however, involve the use of aldehyde-based cross-linking agents, like formaldehyde and glutaraldehyde. During this process, molecular recognition elements of interest, epitopes and/or antigens are preserved using a formaldehyde treatment that produces chemical cross-linking which preserves the cellular features of the tissue. Formaldehyde preserves or fixes tissue or cells predominantly by cross-linking primary amine groups in proteins with other nearby nitrogen atoms in protein or nucleic acids through a —$CH_2$— linkage. The process of tissue fixation however, frequently masks molecular recognition elements, antigens and/or epitopes for which detection is desirable for diagnostic, therapeutic, or prognostic purposes. The result is that the molecular recognition element, antigen and/or epitope of interest may be chemically modified or destroyed by reaction with aldehyde-based fixatives, making detection harder in fixed tissue. Thus, there is a recognized need in the art for improved methods for unmasking and retrieving molecular recognition elements, epitopes, molecules, and antigens of interest. Particularly, the prior art is deficient in methods and compounds that are easily formulated to reverse the aldehyde reaction in fixed tissue. The present invention fulfills this longstanding need and desire in the art.

SUMMARY OF THE INVENTION

In some embodiments, the present disclosure relates to a method for retrieving at least one molecular recognition element in a tissue fixed with aldehyde-based cross-linking agents. In some embodiments, the method comprises preparing a solution comprising at least one aldehyde-scavenging agent. In some embodiments, the solution comprising the aldehyde-scavenging agent further comprises at least one enhancer effective in enhancing aldehyde-scavenging activity of the agent.

In some embodiments, the aldehyde-scavenging agent comprises at least one member selected from the group consisting of beta-dicarbonyl compounds, mono or di-amide scavengers, ethyl alcohols, sulfur containing compounds, mercaptoethylamines, mercaptoethanols, hydrazines, ethanolamines, hydroxylamines, anilines, variation of amines, activated charcoal, phenols, and mixtures and combinations thereof. In some embodiments, the aldehyde-scavenging agent comprises a poly-functional organic species. In some embodiments, the polyfunctional organic species comprises a plurality of the aforementioned compounds in a single molecule.

In some embodiments, the method comprises contacting the tissue fixed with an aldehyde-based cross-linking agent with the aforementioned solution. In some embodiments, a reaction of the aldehyde-scavenging agent with the aldehydes comprising the cross-linking agent retrieves the at least one molecular recognition element.

In some embodiments, the at least one molecular recognition element comprises of nucleic acids, amino acids, peptides, proteins, carbohydrates, lipids, or a combination thereof. In some embodiments, the molecular recognition element is useful for diagnosing a condition or a disease. In some embodiments, the molecular recognition element is a therapeutic target of a condition or a disease. In some embodiments, the molecular recognition element is a prognostic marker of a condition or a disease.

Since aldehyde and aldehyde adducts partially exist in state of reversible equilibrium in the fixed compositions or tissues, aldehyde-scavenging agents in the presence of heating and at optimal pH can shift the equilibrium toward releasing aldehyde, resulting in removal of the reversible aldehyde adducts, thereby unmasking the molecular recognition element, molecule, antigen and/or epitope of interest. Thus, in some embodiments, the method comprises contacting the tissue fixed with the aldehyde-based cross-linking agent with the aforementioned solution; and heating the solution to a temperature ranging from about 60° C. to about 125° C. to reach a reversible equilibrium between aldehyde and aldehyde adducts. In some embodiments, the step of heating comprises heating the solution in a microwave.

In some embodiments, the method further comprises cooling to room temperature; and contacting the tissue fixed with the aldehyde-based cross-linking agent with a second solution. In some embodiments, the second solution comprises of at least one chaotropic agent. In some embodiments, the chaotropic agent is effective in preserving the morphology of the fixed tissue. In some embodiments, the second solution comprises guanidine. In some embodiments, the second solution comprises trifluroethanol. In some embodiments, the second solution comprises a detergent. In some embodiments, the method further comprises detecting the at least one retrieved molecular recognition element. In some embodiments, the step of detecting the at least one molecular recognition element is by staining.

In some embodiments, the present disclosure is also directed to a formulation of a compound or mixture of compounds in a solution useful in the methods as described herein. The compound comprises of at least one aldehyde-scavenging agent or a mixture thereof. In some embodiments, the aldehyde-scavenging agents comprise at least one member selected from the group consisting of beta-dicarbonyl compounds, mono or di-amide scavengers, ethyl alcohols, sulfur containing compounds, mercaptoethylamines, mercaptoethanol, hydrazines, ethanolamines, hydroxylamines, anilines, variation of amines, activated charcoal, phenols, and mixtures and combinations thereof. In some embodiments, the at least one aldehyde-scavenging agent comprises a poly-functional organic species. In some embodiments, the polyfunctional organic species comprises a plurality of the aforementioned compounds in a single molecule. In some embodiments, the solution comprising the aldehyde-scavenging agent further comprises at least one enhancer effective in enhancing aldehyde-scavenging activity of the agent. In some embodiments, the enhancer comprises anilines. In some embodiments, the formulation further comprises a nonionic detergent. In some embodiments, the formulation furthermore comprises a stabilizer.

In some embodiments, the formulation comprises at least one aldehyde scavenging agent, an optional nonionic surfactant and a stabilizing agent in a heated solution at a concentration effective to react with the masked the molecular recognition element.

In some embodiments, the formulation is effective for retrieving molecular recognition elements in a tissue fixed with an aldehyde-based cross-linking agent. In some embodiments, the molecular recognition elements comprise of nucleic acids, amino acids, peptides, proteins, carbohydrates, lipids, or a combination thereof. In some embodiments, the at least one molecular recognition element is useful for diagnosing a condition or a disease. In some embodiments, the at least one molecular recognition element is a therapeutic target of a condition or a disease. In some embodiments, the at least one molecular recognition element is a prognostic marker of a condition or a disease In some embodiments, the present disclosure relates to a kit. In some embodiments, the kit comprises compounds and/or formulations of an aldehyde-scavenging agent useful for the methods disclosed herein. In some embodiments, the kit comprises a stain, dye, antibody or other components useful to detect the unmasked molecular recognition element. In some embodiments, the molecular recognition element comprises of amino acids, proteins, peptides, carbohydrates, lipids, or combinations thereof. In some embodiments, the kit further comprises instructions for using the kit.

The present disclosure is further directed to a method of reducing autofluorescence in tissues caused by heating, using the formulations described herein. The present disclosure further pertains to a method to simultaneously enhance fluorescence intensity after the molecular recognition element retrieval process and remove paraffin from a paraffin embedded sample by applying the optional nonionic surfactant described herein.

In some embodiments, the present disclosure pertains to a kit for retrieving molecular recognition elements in a fixed tissue. In some embodiments, the kit comprises of an aldehyde-scavenging agent. In some embodiments, the kit further comprises of at least one enhancer effective in enhancing aldehyde-scavenging activity of the agent. In some embodiments, the kit comprises of a nonionic surfactant. In some embodiments, the kit comprises of a stabilizing agent. In some embodiments, the kit comprises of a molecular recognition element-detecting agent. In some embodiments, the kit comprises of instructions on using the kit. In some embodiments, the aldehyde-scavenging agent comprises of at least one member selected from the group consisting of beta-dicarbonyl compounds, mono or di-amide scavengers, ethyl alcohols, sulfur containing compounds, mercaptoethylamines, mercaptoethanols, hydrazines, ethanolamines, hydroxylamines, anilines, variation of amines, activated charcoal, phenols, and mixtures and combinations thereof. In some embodiments, the aldehyde-scavenging agent comprises a poly-functional organic species. In some embodiments, the polyfunctional organic species comprises a plurality of the aforementioned compounds in a single molecule.

In some embodiments, the molecular recognition element-detecting agent comprises a stain, a dye or an antibody. In some embodiments, the kit is useful in improving the detection of nucleic acids, amino acids, peptides, proteins, carbohydrates or lipids. In some embodiments, the kit is useful for diagnosing a condition or a disease. In some embodiments, the kit is useful for identifying a therapeutic target of a condition or a disease. In some embodiments, the kit is useful for identifying a prognostic marker of a condition or a disease.

BRIEF DESCRIPTION OF THE DRAWINGS

FIGS. 1A-1B depict the basic structure of substituted maleic anhydrides (FIG. 1A) and maleic or (Z)-2-butenedioic acids (FIG. 1B).

FIGS. 2A-2D illustrates antigen retrieval and immunodetection of collagen IV. Paraformaldehyde fixed tissues were subjected to antigen retrieval using TBST (FIG. 2A), low pH (6.0) sodium citrate (FIG. 2B), pepsin pretreatment (FIG. 2C), and 0.05% maleic anhydride pretreatment (FIG. 2D).

FIGS. 3A-3C illustrate antigen retrieval in fixed tissue via visualization via immunohistochemical methods. Paraformaldehyde fixed cryostat sectioned tissues are visualized using immunofluorescence (FIG. 3A), formaldehyde fixed paraffin embedded tissue is visualized using immunofluorescence (FIG. 3B) and formaldehyde fixed paraffin embedded tissue is visualized using a DAB chromagen by immunohistochemistry (FIG. 3C).

FIGS. 4A-4E compare antigen retrieval in fixed vascular tissue using maleic acid (FIG. 4A), maleic anhydride (FIG. 4B), 2,3-dimethyl maleic anhydride (FIG. 4C), fumaric acid (FIG. 4D), and succinic acid (FIG. 4E).

FIGS. 5A-5E demonstrate retrieval of endothelin-1 (FIG. 5A), VEGF (FIG. 5B), von Willebrand (FIG. 5C), and both alpha-smooth muscle actin (FIG. 5D) and collagen IV (FIG. 5E).

FIGS. 6A-6B illustrate the concentration of protein detected in fixed brain homogenates after heating in increasing concentrations of maleic acid (FIG. 6A) and the corresponding increase in GAPDH in a dot blot comparison (FIG. 6B).

FIG. 7 is a microscope image showing collagen IV staining of blood vessels in paraformaldehyde fixed adult human brain tissue after antigen retrieval.

FIGS. 8A-8B show microscope images showing enhancement of fluorescence after antigen retrieval process by the addition of nonionic surfactant Triton X-100 (FIG. 8B) compared to 0.05% ascorbic acid alone (FIG. 8A).

(FIG. 11D), 5% imidazolidone (FIG. 11E), 5% citric acid (FIG. 11F), 5% guanidine (FIG. 11G), 5% maleic acid (FIG. 11H), 5% Tris buffer at pH=3.5 (FIG. 11I), 5% ascorbic acid (FIG. 11J), 5% hydroxylamine (FIG. 11K) and 5% cysteine (FIG. 11L).

FIGS. 14A-14E show microscope images showing enhanced immunostaining of Collagen IV after antigen retrieval using -Mono or Di-Amide scavengers 2-pyrrolidinone (FIG. 14A), barbituric acid (FIG. 14B), L-asparagine (FIG. 14C), succinimide (FIG. 14D), and tannic acid (FIG. 14E).

FIGS. 16A-16C show microscope images showing enhanced immunostaining of GFAP after antigen retrieval using sulfur containing compounds 1,3,5-triazine-2,4,6-trithiol (FIG. 16A), sodium bisulfite (FIG. 16B), and sodium metabisulfite (FIG. 16C).

FIGS. 22A-22F show microscope images showing enhanced immunostaining of Collagen IV after antigen retrieval using aniline compounds p-anisidine (FIG. 22A), aniline (FIG. 22B), sulfanilic acid (FIG. 22C), 4-ethoxyaniline (FIG. 22D), 4-aminophenol (FIG. 22E), and p-phenylenediamine (FIG. 22F).

FIGS. 24A-24C show immunohistochemical staining of Collagen IV on formalin fixed paraffin embedded mouse brain sections treated with a combination of 1% hydroxylamine alone (FIG. 24A); 1% hydroxylamine and 0.1% 4-aminophenol (FIG. 24B); and 1% hydroxylamine and 0.1% 4-aminophenol (FIG. 24C).

FIGS. 25A-25C show immunohistochemical staining of Collagen IV on formalin fixed paraffin embedded mouse brain sections treated with a combination of 1% hydroxylamine alone (FIG. 25A); 1% Hydroxylamine and 0.1% Aniline (FIG. 25B); and 1% hydroxylamine and 0.5% aniline (FIG. 25C).

FIGS. 26A-26C show immunohistochemical staining of Collagen IV on formalin fixed paraffin embedded mouse brain sections treated with a combination of 0.5% hydroxylamine alone (FIG. 26A); 0.5% hydroxylamine and 0.1% aniline (FIG. 26B); and 0.5% hydroxylamine and 0.5% aniline (FIG. 26C).

FIGS. 29A-29C show immunohistochemical staining of Collagen IV on formalin fixed paraffin embedded mouse brain sections treated with a combination of 0.05% maleic Acid alone (FIG. 29A); 0.05% maleic Acid and 0.1% aniline (FIG. 29B); and 0.05% maleic Acid and 0.5% aniline (FIG. 29C).

DETAILED DESCRIPTION OF THE INVENTION

Figures 9A, 9B, 9C:
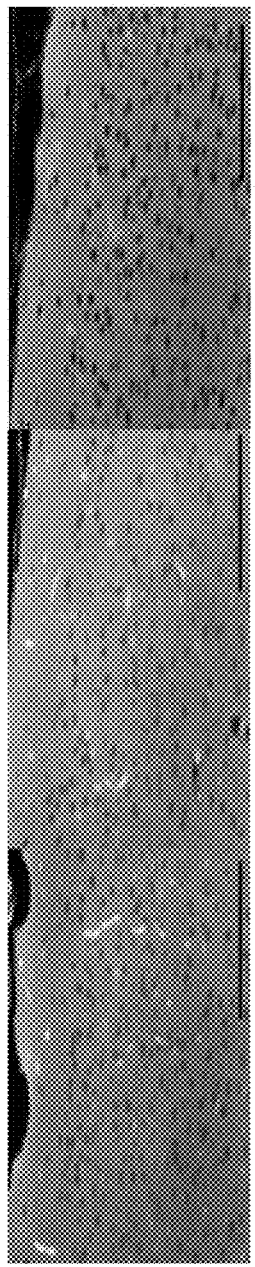
FIGS. 9A-9C show microscope images demonstrating the reduction of autofluorescence in heated tissues with 5% ascorbic acid (FIG. 9C) compared to heated tissue (FIG. 9B) and unheated tissue (FIG. 9A) without 5% ascorbic acid.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "unmasking" refers to retrieving molecular recognition elements, antigens and/or epitopes or molecules for improving the detection of nucleic acids, amino acids, peptides, proteins, lipids, and carbohydrates in a fixed tissue. As used herein, the term "molecular recognition element" refers to a site on a molecule. The molecule may be a peptide, a protein, a carbohydrate, a lipid, a nucleic acid or hybrid of these molecules. The molecular recognition play an important role in a number of biological interactions. Examples of biological interactions include but are not limited to receptor-ligand, antigen-antibody, DNA-protein binding, sugar-lectin, RNA-ribosome, etc. The molecular recognition element may be part of an antigen. An antigen can have multiple molecular recognition elements. The molecular recognition element and antigen be from any species. The molecular recognition element can be on a cell surface receptor, cell surface protein, extracellular protein, intracellular protein, carbohydrate, nucleic acid, lipid, small organic molecules, or other molecules.

The molecular recognition element may comprise post-translational modification of a peptide or modification of carbohydrate, nucleic acid, lipid, or small organic molecules. Examples of post-translational modification include, but are not limited to, phosphorylation, acetylation, alkylation, amidation, biotinylation, formylation, gamma-carboxylation, glutamylation, glycosylation, glycation., hydroxylation, iodination, isoprenylation, lipoylation (e.g. prenylation, myristoylation, farnesylation and geranylgeranylation), ADP-ribosylation, heme attachment, flavin attachment, oxidation, palmitoylation, pegylation, phosphatidylinositol attachment, phosphopantetheinylation, polysialylation, tRNA-mediation addition of amino acids such as arginylation, pyroglutamate formation, sulfation, selenoylation, the covalent linkage to the ISG15 protein, sumoylation, ubiquitination, neddylation, citrullination, deamidation, and eliminylation.

In one embodiment of the present invention, there is provided a method for retrieving antigens and improving the detection of nucleic acids, amino acids, peptides, proteins, carbohydrates, and lipids in a fixed tissue, comprising the steps of preparing a solution of an aldehyde-scavenging agent; and contacting a tissue fixed with an aldehyde-based cross-linking agent with the solution; where a reaction of the aldehyde-scavenging agent with the aldehydes comprising the aldehyde-based cross-linking agent retrieves the antigens and improves detection of the nucleic acids, amino acids, peptides, proteins, carbohydrates or lipids in the fixed tissue.

The compositions and methods disclosed herein are useful for detecting and improving detection of molecules of interest utilizing methods known in the art such as but not limited to immunohistochemistry (IHC), fluorescent in situ hybridization (FISH), Chromogenic in situ hybridization (CISH), RNA in situ hybridization (RNA ISH), and next generation sequencing.

Further to this embodiment the method comprises heating the solution to about 60° C. to about 125° C. for duration of about 30 minutes to about 48 hours, where at this temperature there is a reversible equilibrium between aldehyde and aldehyde adducts. In this further embodiment the aforementioned solution reduces autofluorecence in heated tissues. Further still to this embodiment the method comprises staining the tissue to detect the retrieved molecular recognition element, or antigen or epitope.

In all embodiments, the concentration of the solution of an aldehyde-scavenging agent is about 0.05% to about 30%. Also, the pH of the solution is maintained with in a range specific for the aldehyde scavenging agents. In addition in all embodiments, a representative aldehyde-based cross-linking agent may be formaldehyde or glutaraldehyde.

The aldehyde-scavenging agent are listed in, but not limited to, Table 1. Particularly, the compound may be aminoethanol, N-Methylaminoethanol, 2-(hydroymethyl)piperidine, 2-(hydroxymethyl)pyrrolidine, N-benzylaminoethanol, Amino(bis ethanol), 2-amino-2-methyl-1,3-propanediol; serine, threonine, chitosan, tris(hydroxymethyl) aminomethane, arginine, lysine, glycine, histidine, 5-hydroxytryptophane, carnosine, guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline; 1-amino-2-indole; a polyoxyalkylene amine; a polyamidoamine, anthranilic acid, methyl anthranilate, anthranilamide; o-phenylenediamine; 4-aminobenzoic acid; 3,4-diaminobenzoic acid; hydrazine, N-methylhydrazine, N-phenylhydrazine, methylhydrazide, 2,4-di-nitrophenylhydrazide, urea, allantoin, imidazolidone, phenobarbital, glycoluril, biuret, cysteamine, cysteine, glutathione, sodiumbisulfite, o-mercaptobenzamide, malonamide, acetoacetamide, oxamide, pyroglutamic acid, succinamide, ethylenediamine-N,N'-bisacetoacetamide, N-(2-ethylhexyl)acetoacetamide, N-(3-phenylpropyl) acetoacetamide, a polyamide; a polyesteramide, sorbitol, hexane diol, glucose, cellulose, hydroxycitronellol, dimedone, ascorbic acid, pentane dione, 2-butanone, cyclohexanone, 2,2-dimethyl-,3-dioxan-4,6-dione, 2-pentanone, 5,5-dimethyl-1,3-cyclohexanedione, dehydroacetic acid, 1,3-dihydroxyacetone dimer, methyl gallate, ethyl gallate, propyl gallate, pyrogallol, salicylamide; salicylanilide; 4,5-dihydroxy-2,7-naphthalenedisulfonic acid, citraconic acid, maleic anhydride, 2,3-dimethylmaleic anhydride, 1(E)-2-Butenedioic acid dimethyl ester, 2-sulfanylbut-2-enedioic acid, but-2-enedioic acid, (E)-3-nitroprop-2-enoate, (E)-2,3-dideuteriobut-2-enedioic acid, (Z)-2-methoxybut-2-enedioic acid, (Z)-2-hydroperoxybut-2-enedioic acid, 2-methoxybut-2-enedioic acid, (Z)-2-fluorobut-2-enedioate, 4-oxopent-2-enoic acid, (E)-2,3-dichlorobut-2-enedioic acid, Dichloromaleic acid, (Z)-2-iodobut-2-enedioic acid, (E)-2,3-dideuteriobut-2-enedioic acid, (Z)-2-hydroxy-3-methylbut-2-enedioic acid, 2,3-dideuteriobut-2-enedioic acid, (E)-3-nitrobut-2-enoic acid, but-2-enedioate, (E)-4-chloro-4-oxobut-2-enoate, (E)-2,3-difluorobut-2-enedioate, (E)-4-hydroxy-4-oxobut-2-enoate, hydrogen fumarate, (Z)-2-sulfanylbut-2-enedioic acid, 2,3-Difluorofumaric acid, (E)-4-hydroxy-2-methyl-4-oxobut-2-enoate, mono fluorofumarate, fluorofumaric acid, (Z)-2-chlorobut-2-enedioic acid, 2-hydroperoxybut-2-enedioic acid, Peroxymaleic acid, 2-chloro-3-methylbut-2-enedioic acid, 2-chloro-3-methylbut-2-enedioic acid, 2-Butenedioic acid, [(E)-3-carboxy-1-hydroxyprop-2-enylidene]acid, oxidanium, (E)-2-methylbut-2-enedioate, 2-methylfumarate, citraconic acid, 2,3-dichloromaleic 3,4-dichloro-5-hydroxyfuran-2

(5H)-one, 3-chlorocarbonylacrylic acid ethyl ester, (E)-Ethyl 4-oxopent-2-enoate, [(Z)-3-carboxyprop-2-enoyl]oxidanium, (Z)-but-2-enedioic acid, dimethyl maleate, dimethyl fumarate; cyclodextrins, activated carbon, alumina; silica; amine functionalized silica; talc; zeolites; or a poly functional organic species containing both a primary, or secondary amine group and a carboxylic acid, phenolic, amide, hydroxyl, urea, ester or thiol group, at least one of which reacts with aldehyde; or combinations of any of these compounds.

In some embodiments, the aldehyde-scavenging agents comprise at least one member selected from the group consisting of beta-dicarbonyl compounds, mono or di-amide scavengers, ethyl alcohols, sulfur containing compounds, mercaptoethylamines, mercaptoethanol, mercaptoethanols, hydrazines, ethanolamines, hydroxylamines, anilines, variation of amines, activated charcoal, phenols, and mixtures and combinations thereof. In some embodiments, the aldehyde-scavenging agent comprises a poly-functional organic species. In some embodiments, the polyfunctional organic species comprises a plurality of the aforementioned compounds in a single molecule.

In some embodiments, the present disclosure relates to a method for retrieving at least one molecular recognition element in a tissue fixed with aldehyde-based cross-linking agents. In some embodiments, the method comprises preparing a solution comprising an aldehyde-scavenging agent. In some embodiments, the tissue fixed with an aldehyde-based cross-linking is contacted with the solution comprising the aldehyde-scavenging agent. In some embodiments, a reaction of the aldehyde-scavenging agent with the aldehydes comprising the aldehyde-based cross-linking agent retrieves the at least one molecular recognition element. In some embodiments, the at least one molecular recognition element is useful for diagnosing a condition or a disease. In some embodiments, the molecular recognition element is a therapeutic target of a condition or a disease. In some embodiments, the molecular recognition element is a prognostic marker of a condition or a disease.

In some embodiments, the solution comprising the aldehyde-scavenging agent further comprises at least one enhancer effective in enhancing aldehyde-scavenging activity of the agent.

In some embodiments, the aldehyde-based cross-linking agent is formaldehyde or glutaraldehyde. In some embodiments, the concentration of the aldehyde-scavenging agent in the solution is about 0.05% to about 30%. In some embodiments, the pH of the solution is within a range specific for the aldehyde-scavenging agent or mixture of agents. In some embodiments, the pH of the solution is from about 2.5 to about 11.0. In some embodiments, the pH of the solution is 6. In some embodiments, the method further comprises heating the solution from about 60° C. to about 125° C. In some embodiments, the step of heating the solution reverses equilibrium between aldehyde and aldehyde adducts. In some embodiments, the step of heating the solution is in a microwave oven. In some embodiments, the solution reduces autofluorescence in heated tissues.

In some embodiments, the method further comprises removing and cooling the tissue samples to room temperature. In some embodiments, the method further comprises contacting the tissue with a second solution. In some embodiments, the second solution comprises of at least one chaotropic agent. In some embodiments, the chaotropic agents are selected from the group consisting of butanol, ethanol, guanidinum chloride, lithium percholorate, magnesium chloride, phenol, propanol, sodium dodecyl sulfate, thiorea, and urea. In some embodiments, the second solution comprises guanidine. In some embodiments, the second solution comprises trifluroethanol. In some embodiments, the second solution comprises a non-ionic detergent.

In some embodiments, the method further comprises the step of detecting the at least one molecular recognition element. The detection of the molecular recognition element is by standard methods known in the art and include but are not limited to immunohistochemistry (IHC), fluorescent in situ hybridization (FISH), Chromogenic in situ hybridization (CISH), RNA in situ hybridization (RNA ISH), and next generation sequencing.

In some embodiments, the step of detecting the molecular recognition element comprises contacting the tissue with at least one molecular recognition element-detecting agent. In some embodiments, the molecular recognition element-detecting agent is a stain, a dye, or an antibody. In some embodiments, detecting the molecular recognition element comprises staining the tissue. In some embodiments, the at least one molecular recognition element is derived from peptide, protein, nucleic acid, carbohydrate, lipid, or a combination thereof. In some embodiments, the aldehyde-scavenging agent comprises of at least one member selected from the group consisting of beta-dicarbonyl compounds, mono or di-amide scavengers, ethyl alcohols, sulfur containing compounds, mercaptoethylamines, mercaptoethanol, hydrazines, ethanolamines, hydroxylamines, anilines, variation of amines, activated charcoal, phenols, and mixtures and combinations thereof. In some embodiments, the aldehyde-scavenging agent comprises a poly-functional organic species. In some embodiments, the poly-functional organic species comprises a plurality of the aforementioned compounds in a single molecule.

In some embodiment, the beta-dicarbonyl compounds comprise acetoacetamide and 5,5-dimethyl-1,3-cylohexanedione (dimedone), methyl acetoacetate.

In some embodiment, the mono or di-amide scavengers comprise 2-pyrrolidinone, succinimide, barbituric acid, tannic acid, and L-asparagine.

In some embodiments, the ethyl alcohols comprise polyvinyl alcohol.

In some embodiments, the sulfur containing compounds comprise 1,3,5-triazine-2,4,6-trithiol, sodium bisulfite, and sodium metabisulfite.

In some embodiments, the mercaptoethylamines comprise cysteamine and cysteine.

In some embodiments, the mercaptoethanol comprise ditheotreitrol.

In some embodiments, the hydrazines comprise Girard T reagent, and 2,4-dinitrophenylhydrazine.

In some embodiments, the ethanolamines comprise 2-amino-1-butanol and 2-amino-2-methyl-1,3-propanediol.

In some embodiments, the hydroxylamines comprise hydroxylamine, O-benzylhydroxylamine, O-(carboxymethyl)hydroxylamine, O-ethylhydroxylamine, and O-phenylhydroxylamine.

In some embodiments, the anilines comprise p-anisidine, aniline, sulfanilic acid, 4-aminophenol, 4-ethoxyaniline, p-phenylenediamine, and 2-amino-5-methoxybenzoic acid.

In some embodiments, the variation of amines comprise ammonium bicarbonate and pyridoxamine.

In some embodiments, the phenols comprise coumaric acid and resveratrol.

In some embodiments, the solution comprises hydroxylamine and 4-aminophenol.

In some embodiments, the solution comprises hydroxylamine and aniline.

In some embodiments, the solution comprises O-benzyl-hydroxylamine and aniline.

In some embodiments, the solution comprising the aldehyde-scavenging agent further comprises at least one enhancer effective in enhancing aldehyde-scavenging activity of the agent. In some embodiments, the enhancer comprises at least one aniline.

In some embodiments, the solution comprising the aldehyde-scavenging agent further comprises a nonionic surfactant. In some embodiments, the nonionic surfactant comprises about 0.1% to about 5% of the solution. In some embodiments, the nonionic surfactant removes paraffin from a paraffin embedded sample and enhances fluorescence intensity for detection of the at least one molecular recognition element.

In some embodiments, the solution of the aldehyde-scavenging agent further contains a stabilizing agent. In some embodiments, the stabilizing agent is selected from a preservative, an antifungal agent, an antibacterial agent, a dye, a pigment, anionic detergents, metal salts, antioxidants or a combination thereof.

In some embodiments, the present disclosure pertains to a formulation comprising an aldehyde-scavenging agent in a solution. In some embodiments, the formulation further comprises at least one enhancer effective in enhancing aldehyde-scavenging activity of the agent. In some embodiments, the enhancer comprises at least one aniline.

In some embodiments, the formulation comprises a non-ionic detergent. In some embodiments, the formulation comprises a stabilizer.

In some embodiments, the aldehyde scavenging agent comprises of at least one member selected from the group consisting of beta-dicarbonyl compounds, mono or di-amide scavengers, ethyl alcohols, sulfur containing compounds, mercaptoethylamines, mercaptoethanol, hydrazines, ethanolamines, hydroxylamines, anilines, variation of amines, activated charcoal, phenols, and mixtures and combinations thereof. In some embodiments, the aldehyde-scavenging agent comprises a poly-functional organic species. In some embodiments, the poly-functional organic species comprises a plurality of the aforementioned compounds in a single molecule.

In some embodiments, the formulation is effective for retrieving molecular recognition elements in a tissue fixed with an aldehyde-based cross-linking agent. In some embodiments, the molecular recognition elements comprise nucleic acids, amino acids, peptides, proteins, carbohydrates, lipids, or a combination thereof.

In some embodiments, the aldehyde-scavenging agent is in a heated solution within a pH range specific for the agent or mixtures of agents to be effective as an aldehyde scavenging agent at a concentration effective to react with fixed molecular recognition elements. In some embodiments, the solution is heated to a temperature ranging from about 60° C. to about 125° C. In some embodiments, the pH of the solution is from about 2.5 to about 11.0. In some embodiments, the pH of the solution is 6.

In some embodiments, the concentration of the aldehyde-scavenging agent or mixture of agents in solution is about 0.01% to about 30%.

In some embodiments, the nonionic surfactant is at a concentration of about 0.05% to about 30%.

Representative examples of nonionic surfactants include but are not limited to Cetomacrogol 1000, Cetostearyl alcohol, Cetyl alcohol, cocamide diethanolamine, cocamide monoethanolamine, Decyl glucoside, IGEPAL CA-630, Isoceteth-20, Lauryl glucoside, NP-40, Nonidet P-40, Nonoxynol-9, nonoxynols, Monolaurin, Octaethylene glycol monododecyl ether, Oleyl alcohol, Poloxamers, Poloxamer 407, Polyglycerol polyricinoleate, Polysorbates, Sorbitan monostearate, Sorbitan tristearate; Stearyl alcohol; Triton X-10; Tween 80; octyl-, decyl, dodecyl-glucopyranoside, -maltoside, and deoxycholic acid.

In some embodiments, the stabilizer is a preservative, an antifungal agent, an antibacterial agent, a dye, a pigment, anionic detergents, metal salts, antioxidants or a combination thereof. In one preferred embodiment, the stabilizer is glutathione in a concentration range of about 2 mM to about 400 mM.

In some embodiments, the present disclosure pertains to a kit for retrieving molecular recognition elements and improving the detection of nucleic acids, amino acids, peptides, proteins, carbohydrates or lipids in a fixed tissue. In some embodiments, the kit comprises of at least one aldehyde-scavenging agent. In some embodiments, the kit comprises of an enhancer effective in enhancing the aldehyde-scavenging activity of the aldehyde-scavenging agent. In some embodiments, the kit comprises of an optional nonionic surfactant. In some embodiments, the kit comprises a stabilizing agent. In some embodiments, the kit comprises of an agent for detecting the retrieved molecular recognition element. In some embodiments, the agent for detecting the molecular recognition element comprises a stain, dye or an antibody. In some embodiments, the kit comprises instructions on using the kit. In some embodiments, the aldehyde-scavenging agent comprises of at least one member selected from the group consisting of beta-dicarbonyl compounds, mono or di-amide scavengers, ethyl alcohols, sulfur containing compounds, mercaptoethylamines, mercaptoethanols, hydrazines, ethanolamines, hydroxylamines, anilines, variation of amines, activated charcoal, phenols, and mixtures and combinations thereof.

In another embodiment of the present invention, there is provided a formulation comprising one compound or a mixture of compounds in solution, an optional nonionic surfactant and a stabilizing agent described supra in a heated solution at a concentration effective to react with the masked proteins, within a pH range particular for the compounds to be effective aldehyde scavenging agents, and a temperature range where there is an equilibrium between aldehyde and aldehyde adducts or that enhances the rate of attaining equilibrium between aldehyde and aldehyde adducts. In some embodiments, the heated solution is heated to a temperature ranging from about 60° C. to about 125° C. In some embodiments, the pH of the solution is from about 2.5 to about 11.0. In some embodiments, the pH of the solution is 6.

Particularly, the formulation may comprise the compound or mixture of the compounds at the concentration of about 0.05% to about 30%, and may further contain an optional nonionic surfactant thereof at a concentration of about 0.1 to about 5% and a stabilizing agent in solution comprising water. Examples of the stabilizing agent are, but are not limited to, a preservative, an antifungal agent, an antibacterial agent, a dye, a pigment, anionic detergents, metal salts, antioxidants or a combination thereof.

In yet another embodiment of the present invention there is provided a kit for retrieving a protein of interest in a fixed tissue, comprising an aldehyde scavenging agents as described supra, an optional nonionic surfactant as described supra, a stabilizing agent as described supra, a stain, dye or antibody and instructions on using the kit.

In yet another embodiment of the present invention, there is provided a method for identifying an antigen retrieval agent, comprising the steps of fixing a protein with aldehyde-based cross-linking agent to be tested in an aqueous solution; lyophilizing the solution to obtain fixed protein; adding the fixed protein to a solution containing an agent to be tested as an antigen retrieval agent; heating the solution containing the agent to be tested and the fixed protein; detecting the protein with mass spectrometry; wherein the presence of peaks for the protein indicates the tested agent is an antigen retrieval agent. In this embodiment, the aldehyde-based cross-linking agent comprises about 4% formaldehyde in water. The solution is heated up to a temperature range from about 60° C. to about 125° C. from about 30 minutes to 48 hours.

Provided herein are methods, compounds and kits useful for unmasking and detecting molecular recognition elements, epitopes, antigens, or proteins masked in tissues fixed with aldehyde-based cross-linking agents. Particularly, any compounds that function as aldehyde scavenging agents in a specific pH range are useful for the methods and compositions disclosed herein. The compounds display reactivity towards released aldehyde, formed by hydrolysis of fixative adducts to proteins in tissue formed during aldehyde fixation, shifting the equilibrium between aldehyde and aldehyde adducts toward (form) aldehyde in the fixed tissue.

A representative list of applicable compounds is shown in Table 1.

TABLE 1

| Number | Compound |
|---|---|
| 1 | (E)-2-Butenedioic acid dimethyl ester |
| 2 | 2-sulfanylbut-2-enedioic acid |
| 3 | but-2-enedioic acid |
| 4 | (E)-3-nitroprop-2-enoate |
| 5 | (E)-2,3-dideuteriobut-2-enedioic acid |
| 6 | (Z)-2-methoxybut-2-enedioic acid |
| 7 | (Z)-2-hydroperoxybut-2-enedioic acid |
| 8 | 2-methoxybut-2-enedioic acid |
| 9 | (Z)-2-fluorobut-2-enedioate |
| 10 | 4-oxopent-2-enoic acid |
| 11 | (E)-2,3-dichlorobut-2-enedioic acid |
| 12 | Dichloromaleic acid |
| 13 | (Z)-2-iodobut-2-enedioic acid |
| 14 | (E)-2,3-dideuteriobut-2-enedioic acid |
| 15 | (Z)-2-hydroxy-3-methylbut-2-enedioic acid |
| 16 | 2,3-dideuteriobut-2-enedioic acid |
| 17 | (E)-3-nitrobut-2-enoic acid |
| 18 | but-2-enedioate |
| 19 | (E)-4-chloro-4-oxobut-2-enoate |
| 20 | (E)-2,3-difluorobut-2-enedioate |
| 21 | (E)-4-hydroxy-4-oxobut-2-enoate |
| 22 | Hydrogen fumarate |
| 23 | (Z)-2-sulfanylbut-2-enedioic acid |
| 24 | 2,3-Difluorofumaric acid |
| 25 | (E)-4-hydroxy-2-methyl-4-oxobut-2-enoate |
| 26 | Monofluorofumarate |
| 27 | Fluorofumaric acid |
| 28 | (Z)-2-chlorobut-2-enedioic acid |
| 29 | 2-hydroperoxybut-2-enedioic acid |
| 30 | Peroxymaleic acid |
| 31 | 2-chloro-3-methylbut-2-enedioic acid |
| 32 | 2-Butenedioicacid |
| 33 | [(E)-3-carboxy-1-hydroxyprop-2-enylidene] oxidanium |
| 34 | (E)-2-methylbut-2-enedioate |
| 35 | 2-methylfumarate |
| 36 | Citraconic acid |
| 37 | 2,3-Dichloromaleic acid |
| 38 | 3,4-Dichloro-5-hydroxyfuran-2(5H)-one |
| 39 | 3-Chlorocarbonylacrylic acid ethyl ester |
| 40 | (E)-Ethyl 4-oxopent-2-enoate |
| 41 | O-methylhydroxylamine |
| 42 | [(Z)-3-carboxyprop-2-enoyl]oxidanium |
| 43 | (Z)-but-2-enedioic acid |
| 44 | Dimethyl maleate |

TABLE 1-continued

| Number | Compound |
|---|---|
| 45 | Dimethyl fumarate |
| 46 | aminoethanol |
| 47 | N-Methylaminoethanol |
| 48 | 2-(hydroymethyl)piperidine |
| 49 | 2-(hydroxymethyl)pyrrolidine |
| 50 | N-benzylaminoethanol |
| 51 | Amino(bis ethanol), |
| 52 | 2-amino-2-methyl-1,3-propanediol |
| 53 | serine |
| 54 | threonine |
| 55 | chitosan |
| 56 | tris(hydroxymethyl)aminomethane |
| 57 | amino acids and derivatives including, arginine, lysine, glycine, histidine, 5-hydroxytryptophane, carnosine, |
| 58 | other amine and aniline containing compounds including guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline |
| 59 | 1-amino-2-indole |
| 60 | a polyoxyalkylene amine |
| 61 | a polyamidoamine, anthranilic acid, methyl anthranilate, anthranilamide |
| 62 | o-phenylenediamine |
| 63 | 4-aminobenzoic acid |
| 64 | 3,4-diaminobenzoic acid |
| 65 | hydrazine and hydrazide derivatives including, hydrazine, N-methylhydrazine, N-phenylhydrazine, methylhydrazide, 2,4-di-nitrophenylhydrazide |
| 66 | urea derivatives including urea, allantoin, imidazolidone, phenobarbital, glycoluril, biuret, |
| 67 | thiol derivatives including cysteamine, cysteine, glutathione, sodiumbisulfite, o-mercaptobenzamide, |
| 68 | amide derivatives including malonamide, oxamide, acetoacetamide, oxamide, pyroglutamic acid, succinamide, ethylenediamine-N,N'-bisacetoacetamide, N-(2-ethylhexyl)acetoacetamide, N-(3-phenylpropyl)acetoacetamide, a polyamide |
| 69 | a polyesteramide |
| 70 | hydroxyl compounds including sorbitol, hexane diol, glucose, cellulose, hydroxycitronellol |
| 71 | keto derivatives including, dimedone, ascorbic acid, pentane dione, 2-butanone, cyclohexanone, 2,2-dimethyl-1,3-dioxan-4,6-dione, 2-pentanone, 5,5-dimethyl-1,3-cyclohexanedione, dehydroacetic acid, 1,3-dihydroxyacetone dimer |
| 72 | phenolic derivatives including methyl gallate, ethyl gallate, propyl gallate, pyrogallol, salicylamide; salicylanilide; 4,5-dihydroxy-2,7-naphthalenedisulfonic acid, |
| 73 | solid phase materials including activated carbon, alumina; silica; amine functionalized silica |
| 74 | talc |
| 75 | zeolites |
| 76 | poly functional organic species containing both a primary, or secondary amine group and a carboxylic acid, hydroxyl, urea, phenolic, amide, ester or thiol group, at least one of which is capable of reacting with aldehyde |
| 77 | cyclodextrin compounds |

As described in the Examples, the method provided herein utilizes compounds formulated in solution, for example in water, at a concentration of about 0.05% to 30%. Heating of the fixed tissue at optimized pH range will liberate aldehydes which can react with the compounds in solution to unmask the epitopes and/or antigens of interest. A single aldehyde scavenging compound or a mixture of compounds may be utilized in the formulation. Subsequent to unmasking, one or more molecular recognition element(s) of interest may be detected by methods known in the art including but not limited to staining, immunohistochemistry (IHC), fluorescent in situ hybridization (FISH), Chromogenic in situ hybridization (CISH), RNA in situ hybridization (RNA ISH), and next generation sequencing.

In fixed tissues, these compounds allow for robust detection of epitopes and/or antigens such as vascular proteins and preserve tissue morphology. Moreover, these compounds preserve the detection of DNA in situ using conventional nucleic acid binding dyes such as DAPI, enabling multicolor imaging in histopathological procedures.

Thus, also provided are novel compounds and formulations thereof useful in the methods described herein.

The formulations may contain an optional nonionic surfactant that can simultaneously enhance the fluorescence intensity after unmasking process and remove paraffin from a paraffin embedded sample, eliminating a separate dewaxing step.

Nonionic surfactants include but are not limited to Cetomacrogol 1000, Cetostearyl alcohol, Cetyl alcohol, cocamide diethanolamine, cocamide monoethanolamine, Decyl glucoside, IGEPAL CA-630, Isoceteth-20, Lauryl glucoside, NP-40, Nonidet P-40, Nonoxynol-9, nonoxynols, Monolaurin, Octaethylene glycol monododecyl ether, Oleyl alcohol, Poloxamers, Poloxamer 407, Polyglycerol polyricinoleate, Polysorbates, Sorbitan monostearate, Sorbitan tristearate; Stearyl alcohol; Triton X-10; Tween 80; and octyl-, decyl, dodecyl-glucopyranoside, -maltoside, and deoxycholic acid.

Further provided herein are kits useful for unmasking proteins in fixed tissue.

These kits may comprise one or more novel compounds or the formulations thereof described herein in combination with an antibody or other agent used for detection. Such kits enable the one-step antigen retrieval method for detection of a wide variety of proteins. With the kits, a user may take fixed tissue that has been stored in a variety of conditions, such as paraformaldehyde, formalin, ethanol, or in paraffin blocks, subject these fixed tissues to brief chemical treatments, and then analyze proteins using quantitative techniques such as western blotting and ELISA. These applications enable one of ordinary skill in the art to use vast quantities of archival tissue that currently cannot be used for quantitative protein analysis because of loss of sensitivity due to fixation.

The following examples are given for the purpose of illustrating various embodiments of the invention and are not meant to limit the present invention in any fashion.

Example 1

Compounds

Representative aldehyde-scavenging agents effective to react with aldehyde within a particular pH range include but are not limited to amino ethanol derivatives including, aminoethanol, N-Methylaminoethanol, 2-(hydroymethyl)piperidine, 2-(hydroxymethyl)pyrrolidine, N-benzylaminoethanol, amino(bis ethanol), 2-amino-2-methyl-1,3-propanediol; serine, threonine, chitosan, tris(hydroxymethyl) aminomethane, amino acids and derivatives including, arginine, lysine, glycine, histidine, 5-hydroxytryptophane, carnosine, other amine and aniline containing compounds including guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline; 1-amino-2-indole; a polyoxyalkylene amine; a polyamidoamine, anthranilic acid, methyl anthranilate, anthranilamide; o-phenylenediamine; 4-aminobenzoic acid; 3,4-diaminobenzoic acid; hydrazine and hydrazide derivatives including, hydrazine, N-methylhydrazine, N-phenylhydrazine, methylhydrazide, 2,4-di-nitrophenylhydrazide, urea derivatives including urea, allantoin, imidazolidone, phenobarbital, glycoluril, biuret, thiol derivatives including cysteamine, cysteine, glutathione, sodiumbisulfite, o-mercaptobenzamide, amide derivatives including malonamide, oxamide, acetoacetamide, oxamide, pyroglutamic acid, succinamide, ethylenediamine-N,N'-bisacetoacetamide, N-(2-ethylhexyl)acetoacetamide, N-(3-phenylpropyl)acetoacetamide, a polyamide; a polyesteramide, hydroxyl compounds including sorbitol, hexane diol, glucose, cellulose, hydroxycitronellol, keto derivatives including, dimedone, ascorbic acid, pentane dione, 2-butanone, cyclohexanone, 2,2-dimethyl-I,3-dioxan-4,6-dione, 2-pentanone, 5,5-dimethyl-1,3-cyclohexanedione, dehydroacetic acid, 1,3-dihydroxyacetone dimer, phenolic derivatives including methyl gallate, ethyl gallate, propyl gallate, pyrogallol, salicylamide; salicylanilide; 4,5-dihydroxy-2,7-naphthalenedisulfonic acid, acid and ester derivatives including maleic acid, citraconic acid, maleic anhydride, 2,3-dimethylmaleic anhydride, 1 (E)-2-Butenedioic acid dimethyl ester, 2-sulfanylbut-2-enedioic acid, but-2-enedioic acid, (E)-3-nitroprop-2-enoate, (E)-2,3-dideuteriobut-2-enedioic acid, (Z)-2-methoxybut-2-enedioic acid, (Z)-2-hydroperoxybut-2-enedioic acid, 2-methoxybut-2-enedioic acid, (Z)-2-fluorobut-2-enedioate, 4-oxopent-2-enoic acid, (E)-2,3-dichlorobut-2-enedioic acid, Dichloromaleic acid, (Z)-2-iodobut-2-enedioic acid, (E)-2,3-dideuteriobut-2-enedioic acid, (Z)-2-hydroxy-3-methylbut-2-enedioic acid, 2,3-dideuteriobut-2-enedioic acid, (E)-3-nitrobut-2-enoic acid, but-2-enedioate, (E)-4-chloro-4-oxobut-2-enoate, (E)-2,3-difluorobut-2-enedioate, (E)-4-hydroxy-4-oxobut-2-enoate, hydrogen fumarate, (Z)-2-sulfanylbut-2-enedioic acid, 2,3-Difluorofumaric acid, (E)-4-hydroxy-2-methyl-4-oxobut-2-enoate,
monofluorofumarate, fluorofumaric acid, (Z)-2-chlorobut-2-enedioic acid, 2-hydroperoxybut-2-enedioic acid, Peroxymaleic acid, 2-chloro-3-methylbut-2-enedioic acid, 2-chloro-3-methylbut-2-enedioic acid, 2-Butenedioic acid, [(E)-3-carboxy-1-hydroxyprop-2-enylidene]oxidanium, (E)-2-methylbut-2-enedioate, 2-methylfumarate, citraconic acid, 2,3-dichloromaleic acid, 3,4-Dichloro-5-hydroxyfuran-2(5H)-one, 3-chlorocarbonylacrylic acid ethyl ester, (E)-Ethyl 4-oxopent-2-enoate, [(Z)-3-carboxyprop-2-enoyl]oxidanium, (Z)-but-2-enedioic acid, dimethyl maleate, dimethyl fumarate, cyclodextrins, solid phase materials including activated carbon, alumina; silica; amine functionalized silica; talc; zeolites; or a poly functional organic species containing both a primary, or secondary group and a carboxylic acid, hydroxyl, urea, phenolic, amide, ester or thiol group, at least one of which is capable of reacting with aldehyde; or combinations of any of these compounds.

Example 2

Antigen Retrieval in Formaldehyde Fixed Tissue: General Method

Small amounts of one or a mixture of compounds, for example, from Table 1 are added to water, in a 0.05%-5% concentration. The solution is heated to about 70° C. to about 95° C. for about 30 minutes. The ensuing chemical reaction enables the unmasking or retrieval of the chemical epitopes. The formaldehyde-fixed tissue is placed into the heated solution for about 30 minutes and then washed. The tissues can then be stained to detect the protein of interest.

Superior antigen retrieval and immunodetection of collagen IV, a vascular protein, in paraformaldehyde fixed tissues was demonstrated using maleic anhydride (FIGS. 2A-2D).

Example 3

Antigen Retrieval is Cross Compatible with Different Immunohistochemical Methods The method of antigen retrieval is compatible and enhances visualization of proteins in multiple forms of processed tissues. Micrographs illustrate an enhanced visualization in paraformaldehyde fixed cryostat sectioned tissues visualized using immunofluorescence, and formaldehyde fixed paraffin embedded tissue visualized using a DAB chromagen by immunohistochemistry (FIGS. 3A-3D).

Example 4

Maleic Acid, Maleic Anhydride and 2,3-Dimethylmaleic Anhydride as Antigen Retrieval Agents compared to Succinic Anhydride Paraformaldehyde fixed tissue samples are heated in solutions of compounds prepared as described in Example 1 and the blood vessels in the tissue are visualized. In maleic acid (FIG. 4A), maleic anhydride (FIG. 4B), and 2,3-dimethylmaleic anhydride related tissue demonstrates successful antigen retrieval with visualization of the blood vessels (FIG. 4C). FIG. 4D shows that the cis-configuration at the alpha, beta double bond of these compounds yields a substantially higher activity than treatment with fumaric acid, which contains a trans-configuration demonstrates a significant reduction in activity. In distinct contrast, FIG. 4E demonstrates no vasculature is visible in the succinic anhydride treated tissue. This demonstrates that the cis-configuration is superior for antigen retrieval.

Example 5

Vascular Antigen Retrieval in Adult Mouse Brain Tissue with Maleic Anhydride 12-month-old C 57 black 6J mice and six month were housed under controlled environment conditions on a conventional 12 hour light dark cycle. Following sacrifice, brains were post-fixed in 4% paraformaldehyde for 72 hours at 4° C. and then transferred to a 70% ethanol solution where they were stored at 4° C. Tissue was paraffin-processed using convention dehydration and embedding, and then sectioned at 5 μm intervals. Cryosectioned tissue was embedded in Optimal cutting temperature compound (Tissue-Tek) and then frozen at −80° C.; 50 μm sections were cut on a cryostat (Leica). In studies where different processing studies were conducted, adjacent sections were used for comparison.

For sections incubated in carbonic anhydride solution, 50 μm sections were incubated in PBS containing 0.2% Triton X-100 three times for ten minutes each, and then slices were immersed for 45 minutes in a 0.05% maleic anhydride (Sigma Aldrich) solution in distilled water, prewarmed to 95° C. Sections were cooled to room temperature and then washed in four changes of PBS for 15 min, prior to processing through immunohistochemistry.

Treatment of formaldehyde fixed tissues with maleic anhydride was used to unmask a broad variety of vascular-associated antigens normally masked by aldehyde-based fixation. Endothelin-1, VEGF, von Willebrand, and using double labeling, alpha-smooth muscle actin and collagen IV (FIGS. 5A-5D), were unmasked using antibodies that have been reported to work in tissue.

Example 6

Antigen Retrieval from Tissue Homogenates from Formaldehyde Fixed Brain Tissue

Due to its ability to crosslink and modify tissues, aldehyde-based fixation significantly impairs or prevents the use of fixed tissues in quantitative techniques to detect proteins, such as the Lowry and BCA assays, dot blotting or western blotting. This example demonstrates the utility of this invention in recovery of detectable protein. As shown in FIG. 6A, when formaldehyde-fixed protein homogenates from brain are heated in the presence of varying concentrations of maleic acid, the protein levels that are quantifiable by the BCA assay increases nearly 8-fold, indicating an increase in available free amino acids. However, unfixed protein that is similarly heated with maleic acid is readily detected by BCA and the concentration remains constant (data not shown). FIG. 6B is a dot blot comparison of detectable GAPDH protein, demonstrating that the use of these compounds leads to a significant and detectable increase of specific proteins. Formaldehyde treated tissues were treated with concentrations of maleic acid from 1.6% to 12.8% with heating at 95° C. for 30 minutes, demonstrating a parallel increase in the detection of GAPDH. In contrast, GAPDH was undetectable in untreated formaldehyde cross-linked tissue.

Example 7

Antigen Retrieval in Adult Human Brain Vasculature

Paraformaldehyde fixed paraffin embedded tissue from adult human brain is treated with 2,3-dimethylmaleic acid as an antigen retrieval method as described. Blood vessels were detected using Collagen IV (FIG. 7).

Example 8

Fluorescent Enhancement after Antigen Retrieval Process with the Addition of Triton Paraformaldehyde fixed paraffin embedded brain tissue is deparaffinized, heated to 70° C. for minutes for 30 minutes in solution, and then blood vessels are detected using Collagen IV (FIG. 8A-8B). Images are captured using 488 nM excitation. Addition of 0.5% Triton X-100 to a 5.0% ascorbic acid solution results in significant improvement in staining evenness and intensity (FIG. 8A) over the sample without Triton X-100 (FIG. 8B).

Example 9

Autofluorescence Reduction by Treatment of Formulation for Antigen Retrieval

Paraformaldehyde fixed paraffin embedded brain tissue is deparaffinized, heated to 70° C. for minutes for 30 minutes in solution, and images are captured using 488 nM excitation (FIG. 9A-9C). Images are captured at same exposure and time. Compared with unheated tissue (FIG. 9A), tissue heated only in water (FIG. 9B) displayed enhanced tissue autofluorescence. Addition of 5% ascorbic acid under the same conditions dramatically reduces visible autofluorescence (FIG. 9C).

Example 10

Increased Stability of Compounds with the Addition of Glutathione

Figures 10A, 10B, 10C:
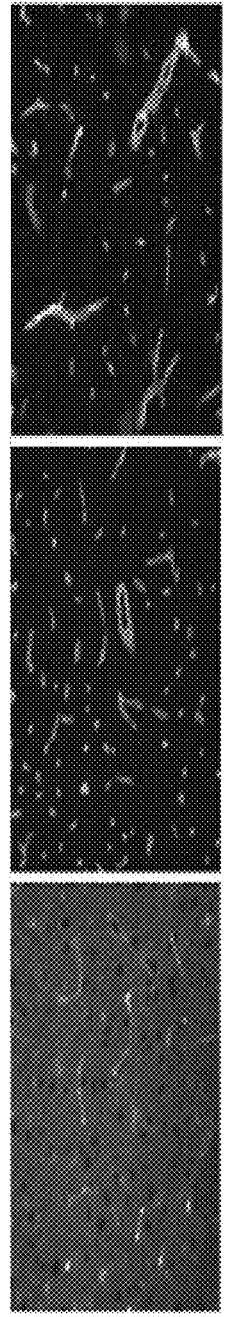
FIGS. 10A-10C show paraformaldehyde fixed paraffin embedded brain tissue is deparaffinized heated to 70° C. for 30 minutes with 2.8 mM glutathione (FIG. 10A), 5% ascorbic acid (FIG. 10B) and 2.8 mM glutathione+5% ascorbic acid (FIG. 10C) in solution.

Paraformaldehyde fixed paraffin embedded brain tissue is deparaffinized, heated to 70° C. for 30 minutes in solution, and images captured using 488 nM excitation with 20× magnification (FIG. 10A-10C). Images are captured at the same exposure and time at 20× magnification. Glutathione did not have an effect on tissue without the presence of ascorbic acid (FIG. 10A), compared to tissue heated in 5% ascorbic acid (negative control) (FIG. 10B). The addition of 2.8 mM glutathione to 5% ascorbic acid (FIG. 10C) increased stability of ascorbic acid while preserving staining.

Example 11

Antigen Retrieval (Angiotensin I) Using Different Aldehyde Scavenging Compounds

Angiotensin I is treated with formalin at room temperature for 48 hours. Compounds including water at pH=3.5 (FIG. 11C), water at pH=5.5 (FIG. 11D), 5% imidazolidone (FIG. 11E), 5% citric acid (FIG. 11F), 5% guanidine (FIG. 11G), 5% maleic acid (FIG. 11H), Tris buffer at pH=3.5 (FIG. 11I), ascorbic acid (FIG. 11J), Hydroxylamine (FIG. 11K), cysteine (FIG. 11L) are respectively heated with the treated Angiotensin I at 95° C. for 45 minutes to test the ability of antigen retrieval for each compound. Mass-spectrometry is used to analyze the compositions of the Angiotensin I before and after treatment by each compound. Samples of Angiotensin I before (FIG. 11A) and after (FIG. 11B) formalin treatments are used as the controls for the experiment. The results of the test are shown in FIG. 11A-11L). Peaks at m/z 1296 represent unmodified Angiotensin I. Peaks at m/z 1308 represent Angiotensin I with 1 methylene unit. Peaks at m/z 1320 represent Angiotensin I with 2 methylene units. Peaks at m/z 1338 represent Angiotensin I with 1 methylene unit and 1 hydroxymethylene group. Peaks at m/z 1350 represent Angiotensin I with 2 methylene units and 1 hydroxymethylene group.

Figure 11A:
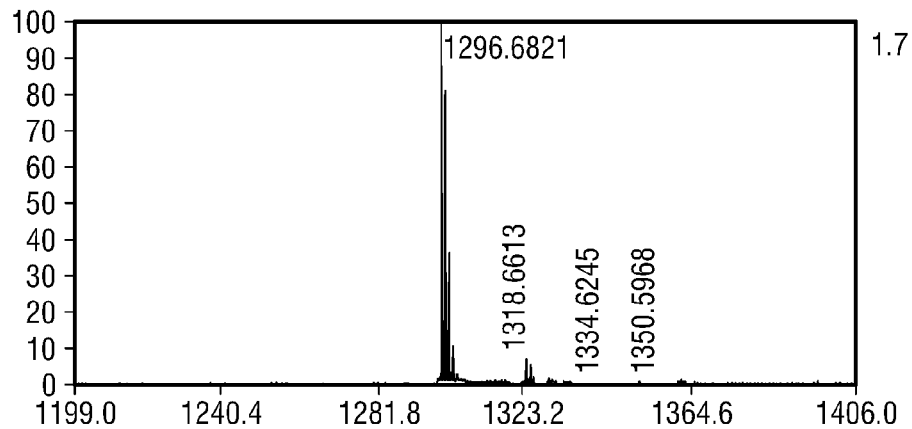
FIGS. 11A-11L show mass-spectrometry results for antigen retrieval of formalin treated Angiotensin I (FIGS. 11A-11B) using water at pH=3.5 (FIG. 11C), water at pH=5.5
Figure 11B:
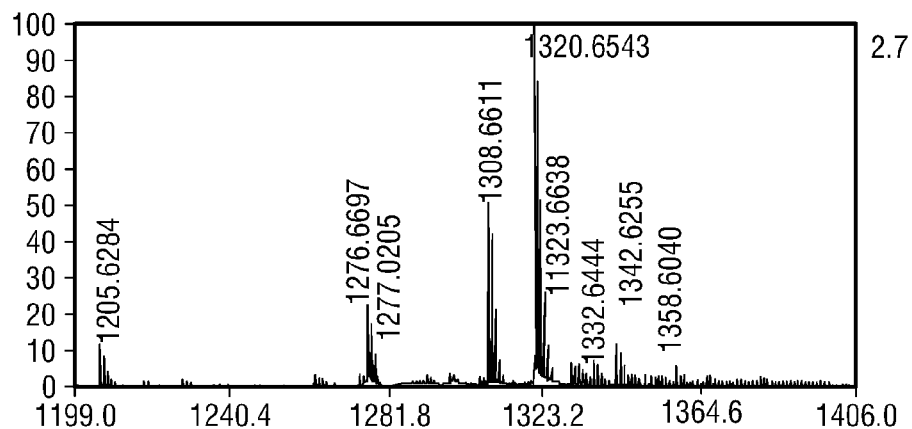
Figure 11C:
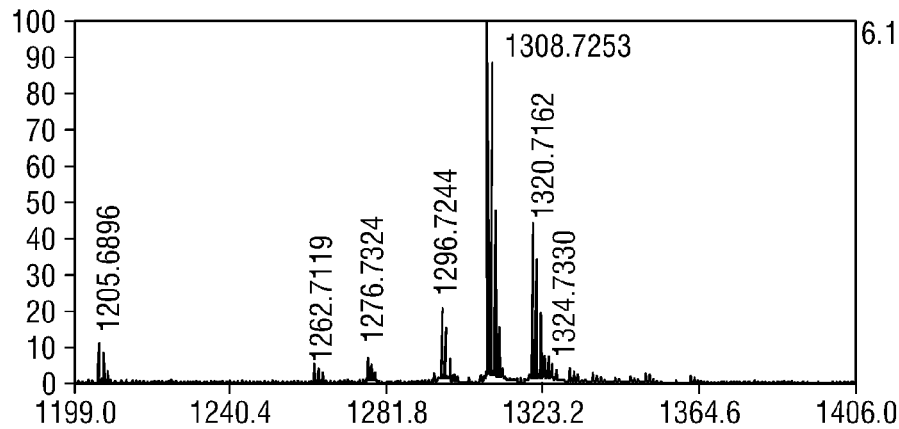
Figure 11D:
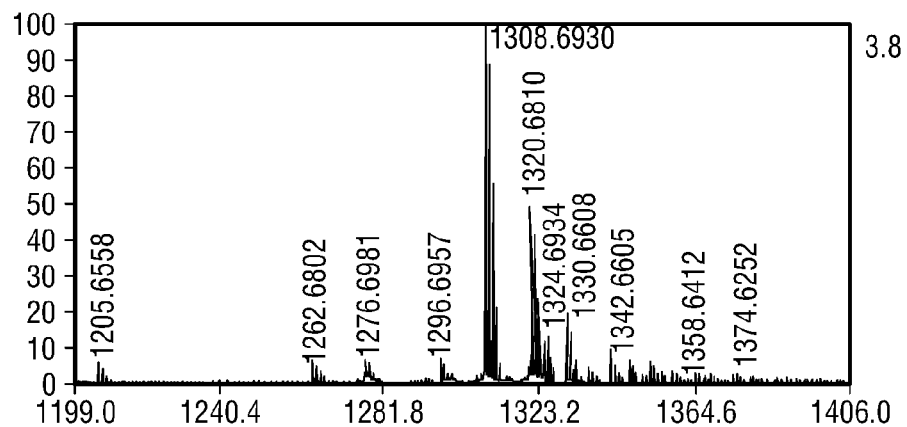
Figure 11E:
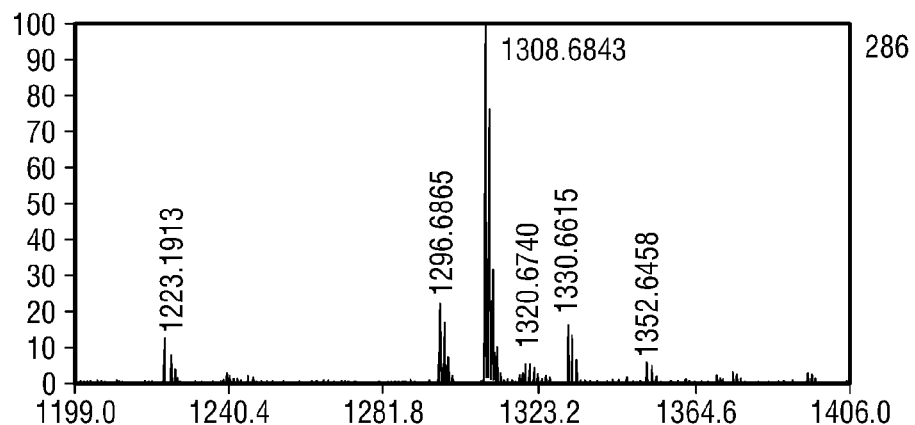
Figure 11F:
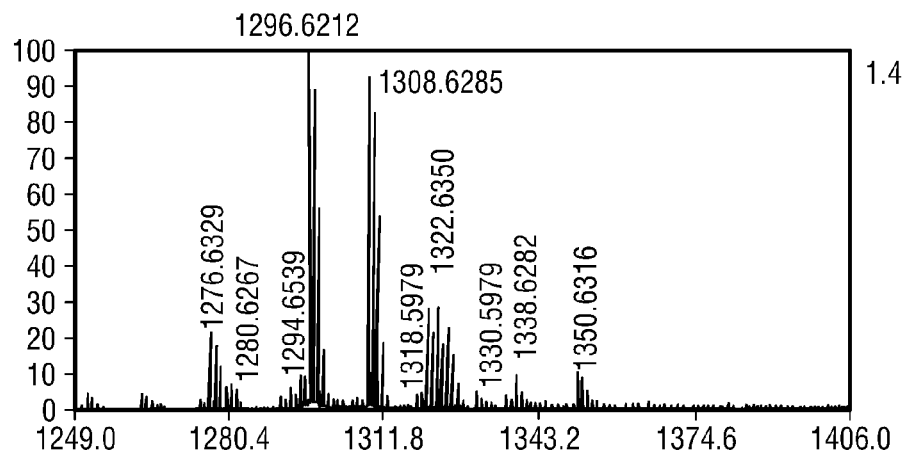
Figure 11G:
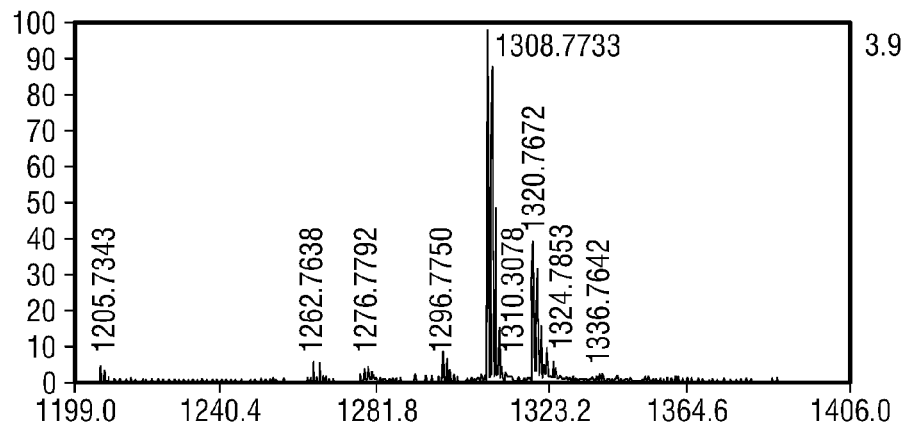
Figure 11H:
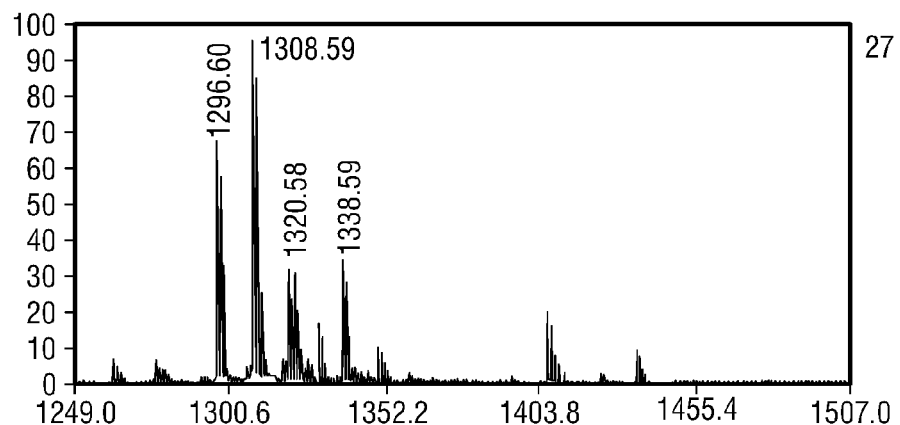
Figure 11I:
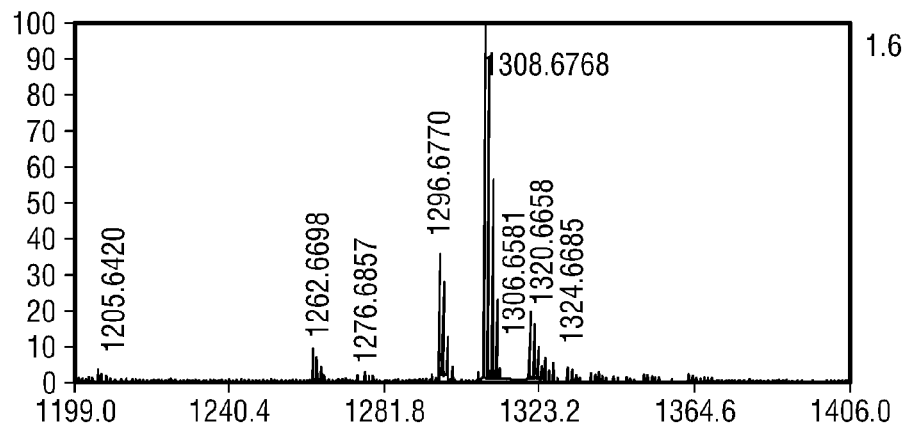
Figure 11J:
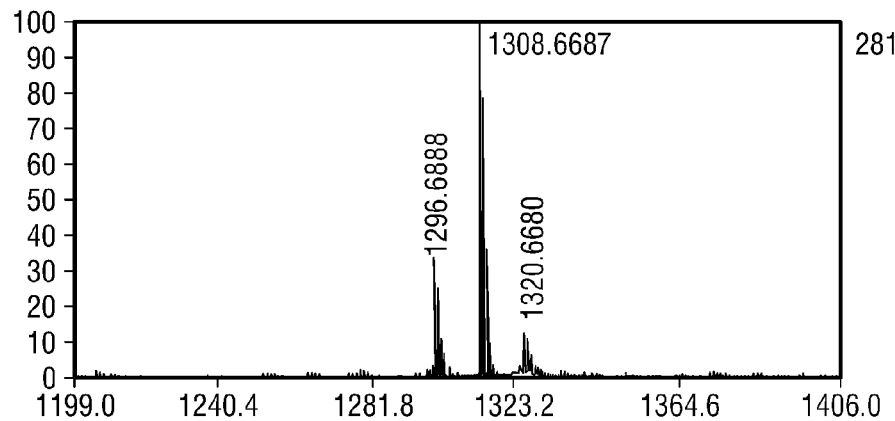
Figure 11K:
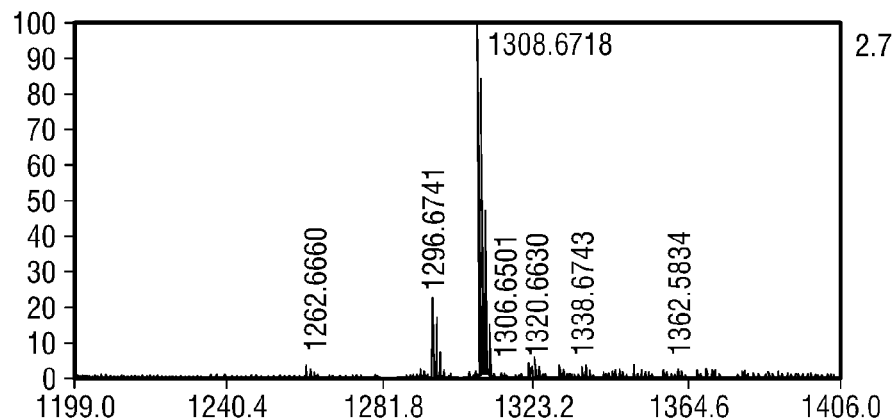
Figure 11L:
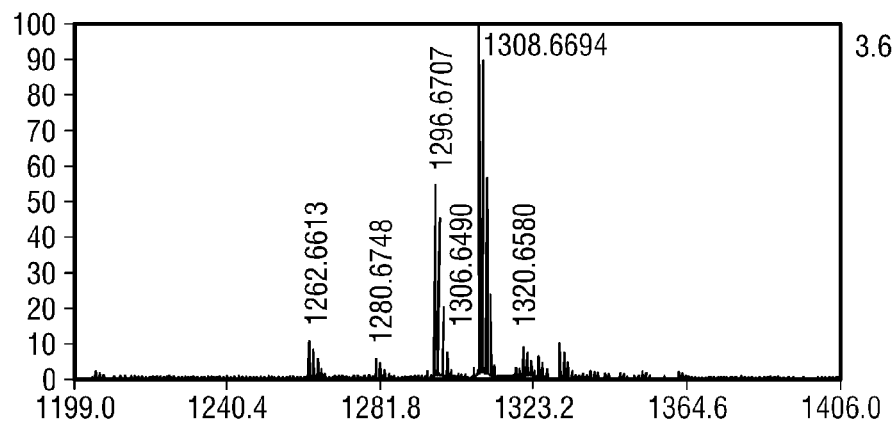

FIG. 11A-11B depicts the complete conversion of Angiotensin I to formalin-adducts. FIG. 11C-11D reveals that water at pH=3.5 has shown the ability of retrieval of formalin-adducts, but water at pH=5.5 exhibits almost no retrieval of formalin adducts. Comparisons of FIGS. 11B, 11D and 11G demonstrate that both 5% maleic acid and 5% imidazolidone are able to significantly reduce the amount of Angiotensin I with 2 methylene groups (m/z 1320), resulting in higher content of unmodified Angiotensin I (m/z 1296). Comparisons between FIG. 10B and FIG. 10F indicate that 5% citric acid (45 minutes, 95° C.) is able to significantly reduce the content of both Angiotensin I with 2 methylene units (m/z 1320) and Angiotensin with 1 methylene unit and 1 hydroxymethylene group (m/z 1338). FIG. 11G shows 5% guanidine exhibits minimal ability to retrieve Angiotensin I with 1 methylene unit and 1 hydroxymethylene group (m/z 1338), and does not exhibit any impact on the content of Angiotensin I with 2 methylene units (m/z 1320). Further, comparisons between FIG. 11B and FIGS. E and 11I-11L show 5% citric acid, 5% Tris buffer at pH=3.5, 5% ascorbic acid, 5% hydroxylamine and 5% cysteine all exhibits significant retrieval of formalin adducts.

Example 12

Figure 12A:
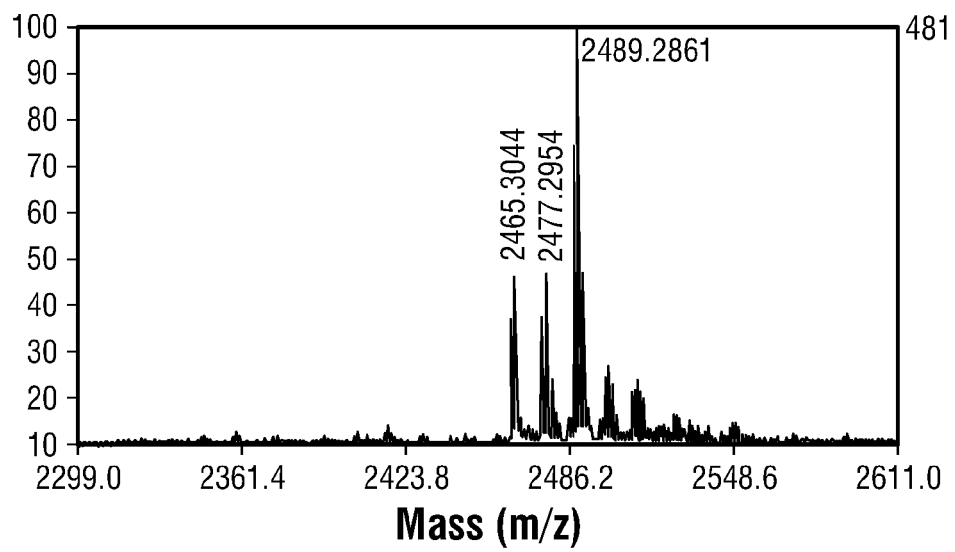
FIGS. 12A-12D show mass-spectrometry results for antigen retrieval of formalin treated ACTH (FIG. 12A) using 5% maleic acid (FIG. 12B), 5% ascorbic acid (FIG. 12C) and water (FIG. 12D). ACTH is treated with formalin at room temperature for 48 hours.
Figure 12B:
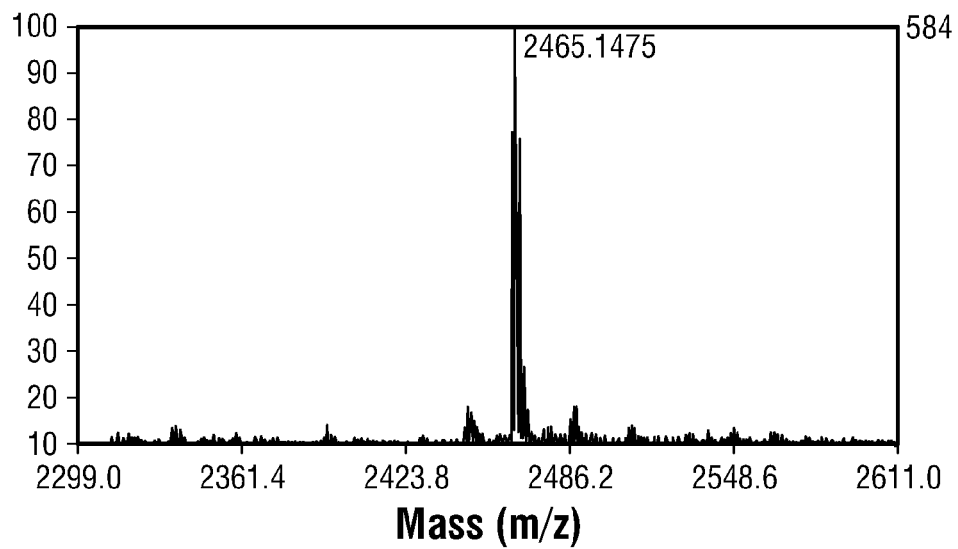
Figure 12C:
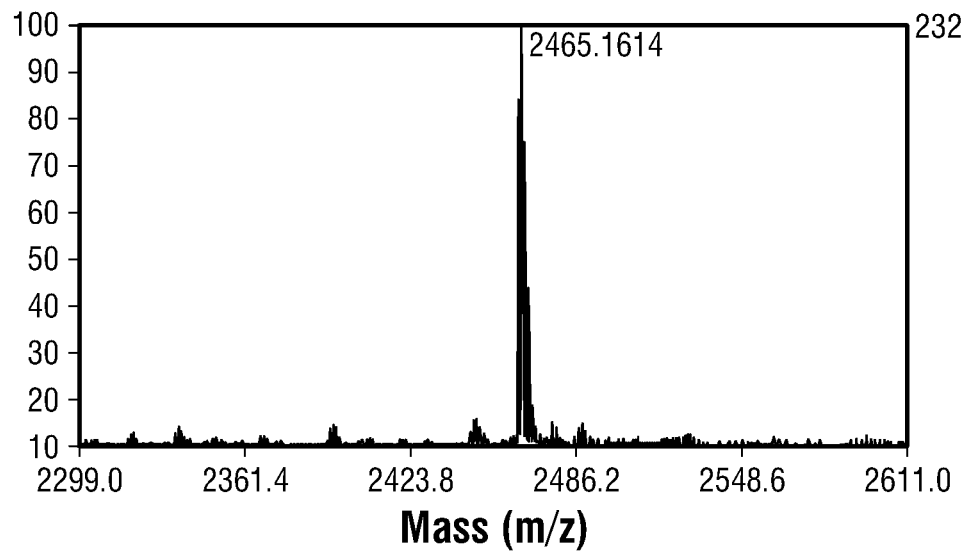
Figure 12D:
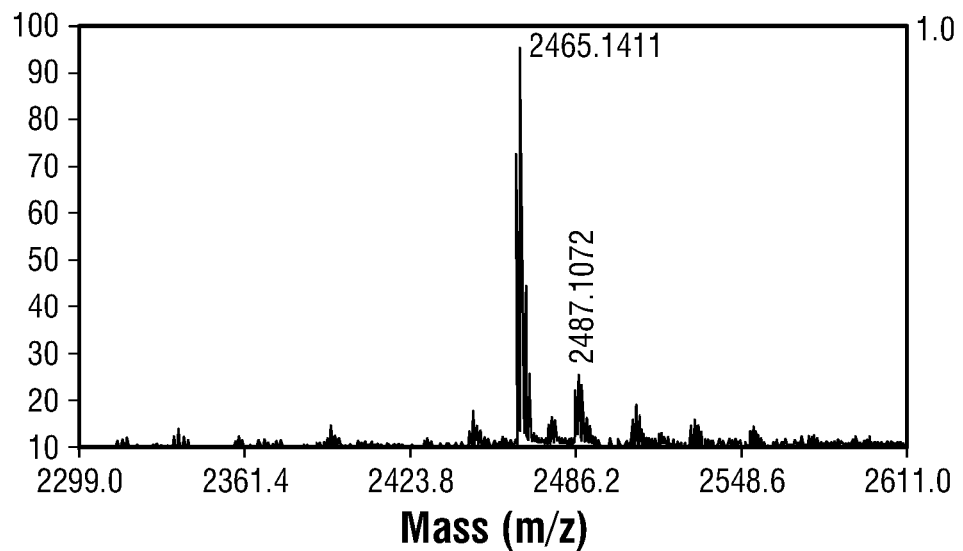
Figure 13B:
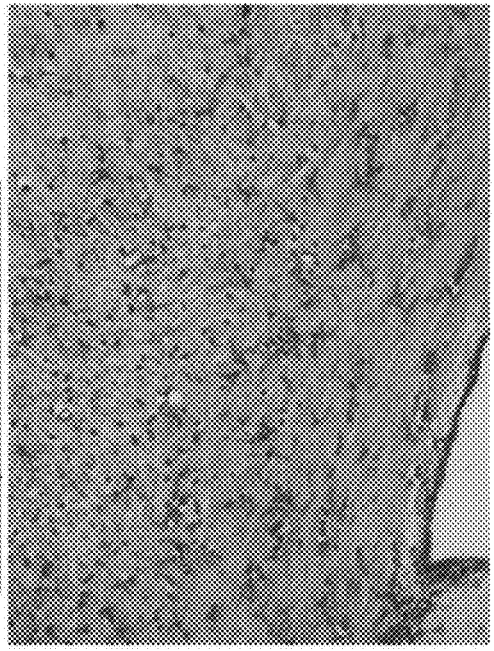
FIGS. 13A-13B show microscope images showing enhanced immunostaining of Collagen IV after antigen retrieval using beta-dicarbonyl compounds acetoacetamide (FIG. 13A) and 5,5-dimethyl-1,3-cylohexanedione (dimedone) (FIG. 13B).
Figure 13A:
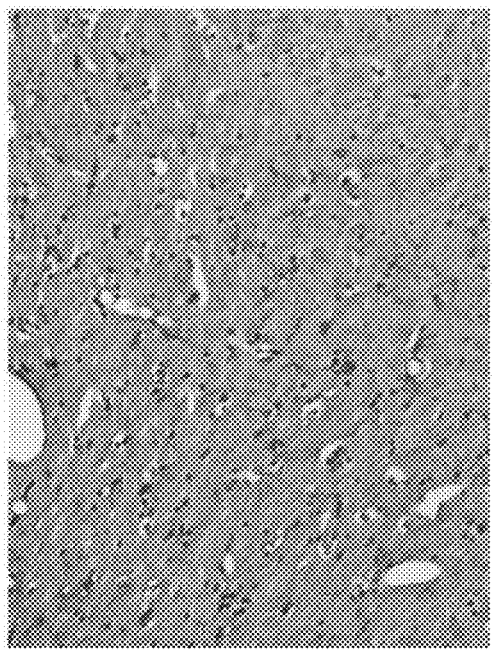
Figure 15:
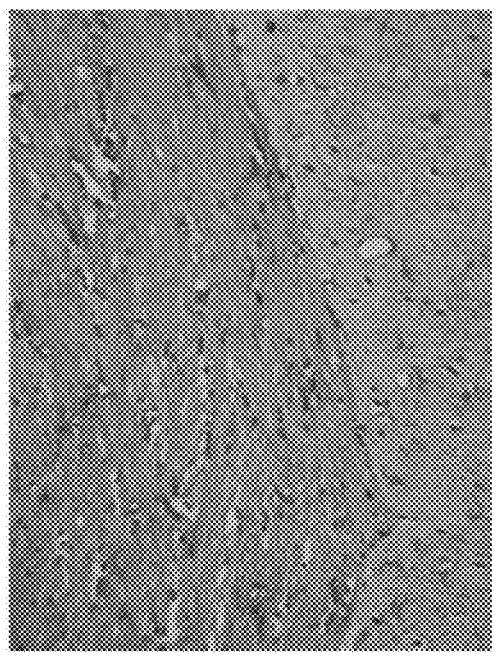
FIG. 15 shows microscope images showing enhanced immunostaining of GFAP after antigen retrieval using ethyl alcohols comprising polyvinyl alcohol.
Figure 17B:
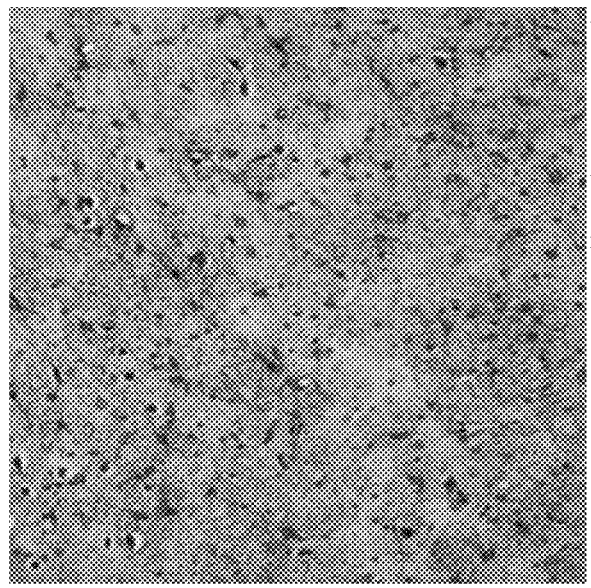
FIGS. 17A-17B show microscope images showing enhanced immunostaining of GFAP after antigen retrieval using mercaptoethylamines compounds cysteamine (FIG. 17A) and cysteine (FIG. 17B).
Figure 17A:
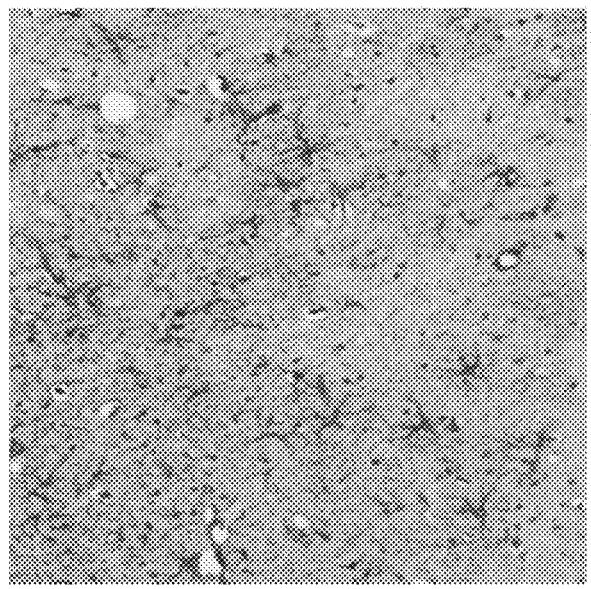
Figure 18B:
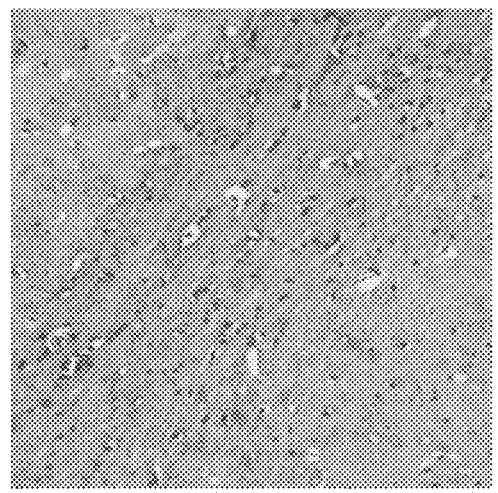
FIGS. 18A-18B show microscope images showing enhanced immunostaining of Collagen IV and GFAP after antigen retrieval using hydrazine compounds Girard T Reagent (FIG. 18A) and 2,4-Dinitrophenylhydrazine (FIG. 18B).
Figure 18A:
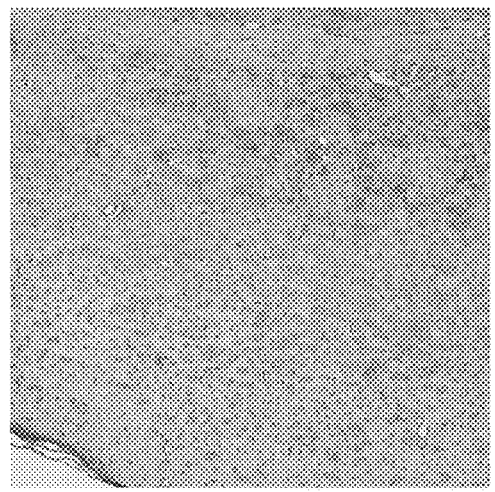
Figure 19:
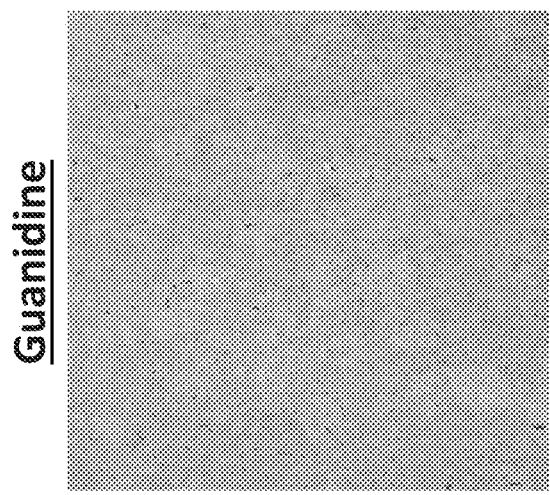
FIG. 19 shows microscope images showing enhanced immunostaining of Collagen IV after antigen retrieval using guanidine.
Figures 20A, 20B:
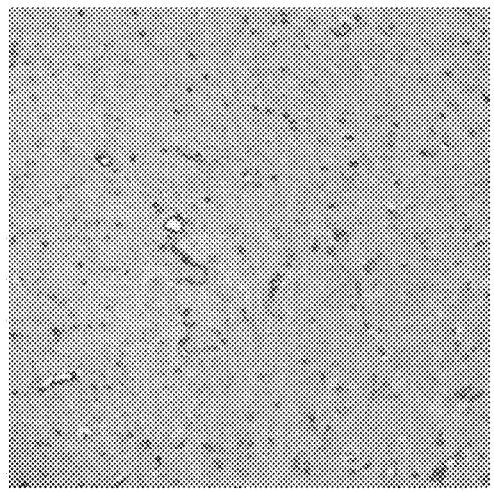
FIGS. 20A-20B show microscope images showing enhanced immunostaining of Collagen IV after antigen retrieval using ethanolamine compounds 1-amino-1-butanol (FIG. 20A) and 2-amino-2-methyl-1,3-propanediol (FIG. 20B).
Figure 21A:
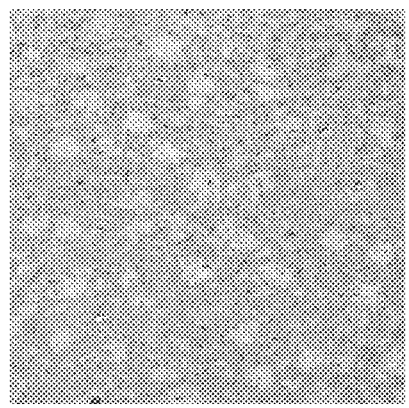
FIGS. 21A-21D show microscope images showing enhanced immunostaining of Collagen IV after antigen retrieval using hydroxylamine compounds O-ethylhydroxylamine (FIG. 21A), hydroxylamine (FIG. 21B), O-(carboxymethyl)hydroxylamine (FIG. 21C), and O-benzylhydroxylamine (FIG. 21D).
Figure 21D:
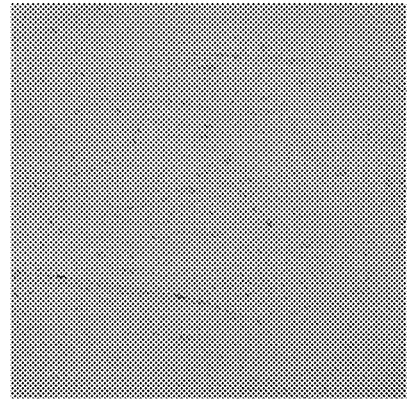
Figure 21C:
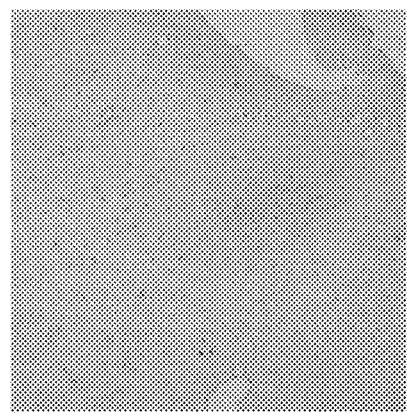
Figure 21B:
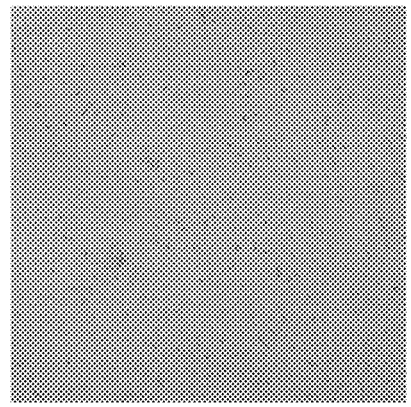
Figure 23B:
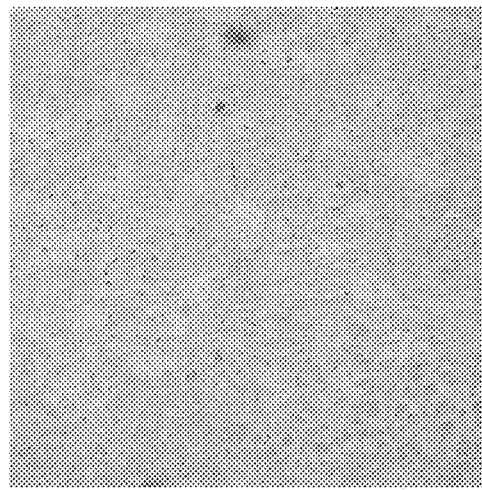
FIGS. 23A-23B show microscope images showing enhanced immunostaining of Collagen IV after antigen retrieval using variation of amines ammonium bicarbonate (FIG. 23A) and pyridoxamine (FIG. 23B).
Figure 23A:
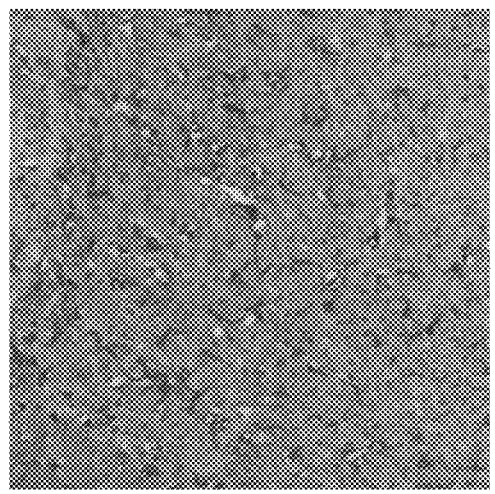
Figure 27A:
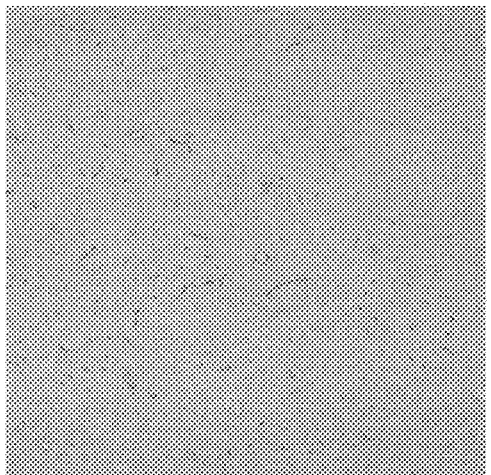
FIGS. 27A-27C show immunohistochemical staining of Collagen IV on formalin fixed paraffin embedded mouse brain sections treated with a combination of 1% O-benzylhydroxylamine HCl alone (FIG. 27A); 1% O-benzylhydroxylamine HCl and 0.1% aniline (FIG. 27B); and 1% O-benzylhydroxylamine HCl and 0.5% aniline (FIG. 27C).
Figure 27B:
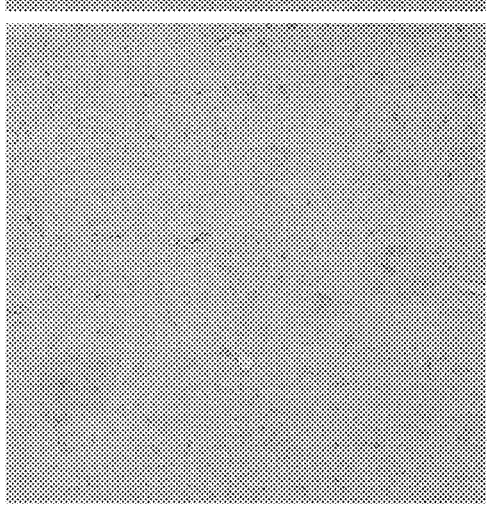
Figure 27C:
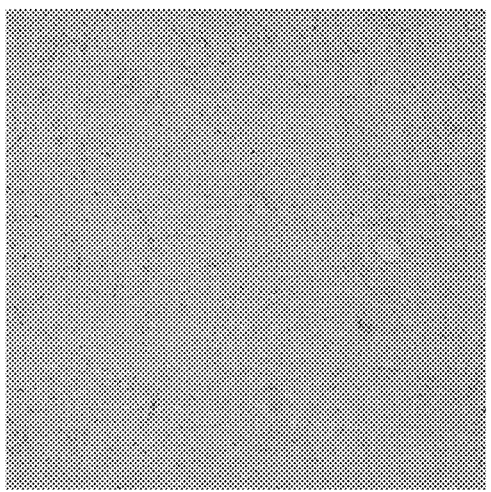
Figure 28A:
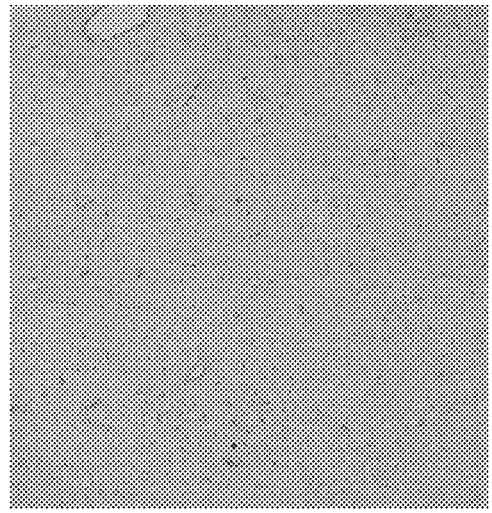
FIGS. 28A-28C show immunohistochemical staining of Collagen IV on formalin fixed paraffin embedded mouse brain sections treated with a combination of 0.5% O-benzylhydroxylamine HCl alone (FIG. 28A); 0.5% O-Benzylhydroxylamine HCl and 0.1% aniline (FIG. 28B); and 0.5% O-benzylhydroxylamine HCl and 0.5% aniline (FIG. 28C).
Figure 28B:
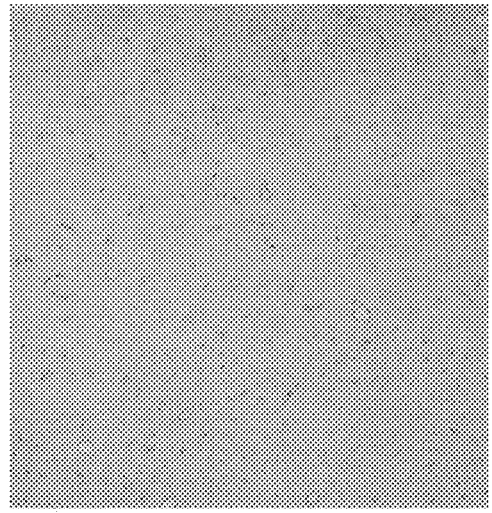
Figure 28C:
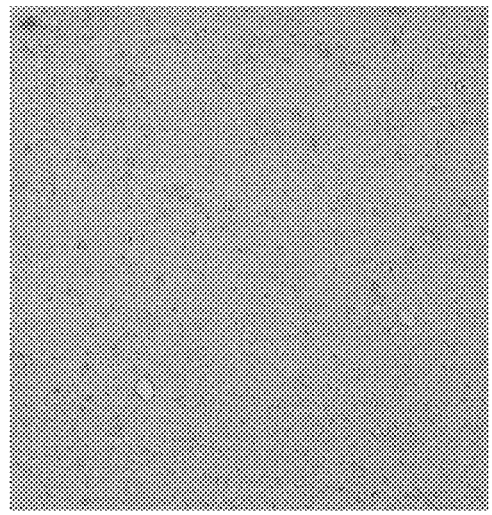
Figure 30:
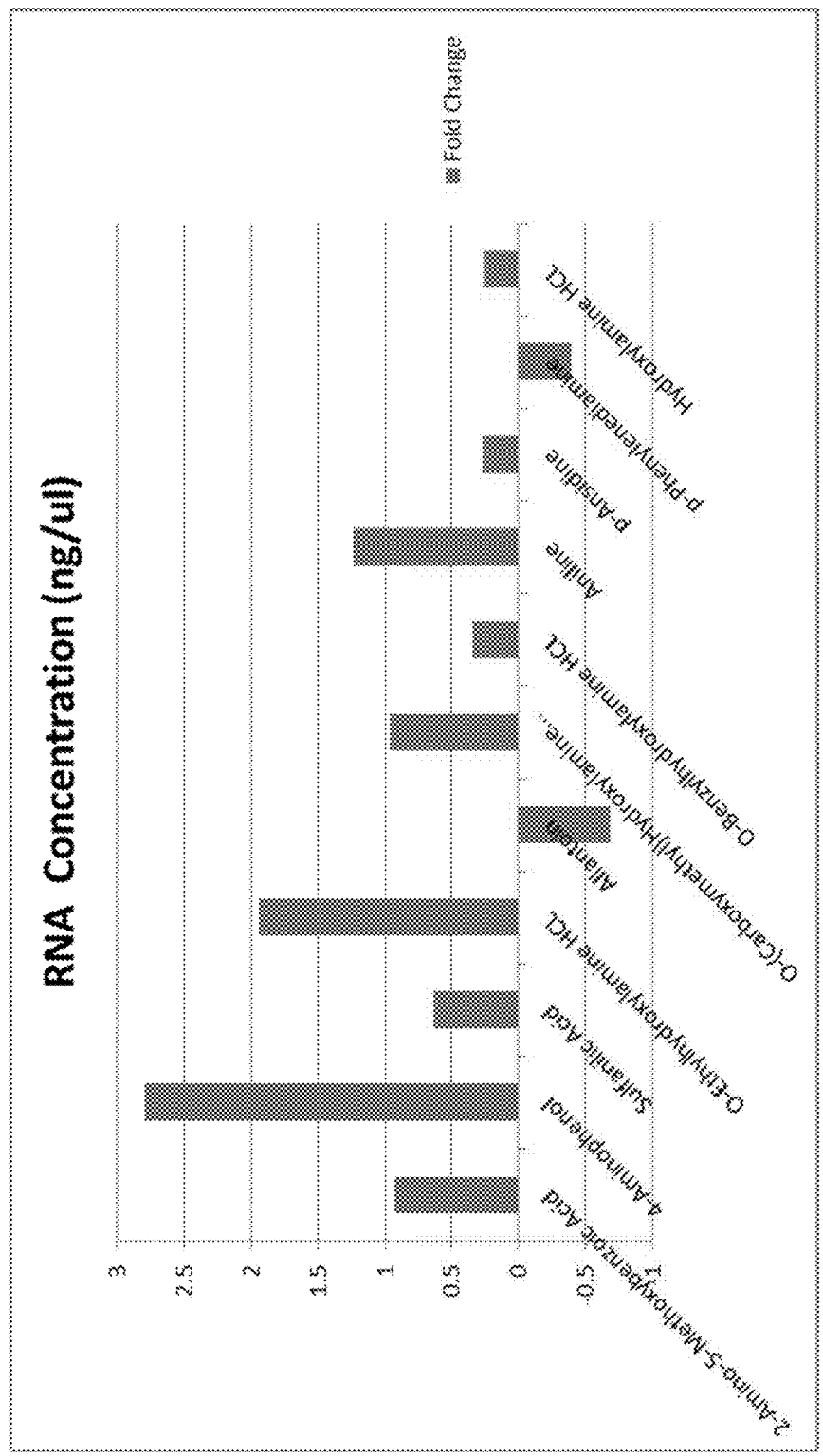
FIG. 30 show enhanced recovery of RNA from formalin-fixed paraffin-embedded tissue samples using different aldehyde scavenging agents 2-amino-5-methoxybenzoic acid, 4-aminophenol, sulfanilic acid, O-ethylhydroxylamine HCl, O-(carboxymethyl)hydroxylamine, O-benzylhydroxylamine, aniline, p-ansidine, and hydroxylamine compared to control.
Figures 31A, 31B, 31C:
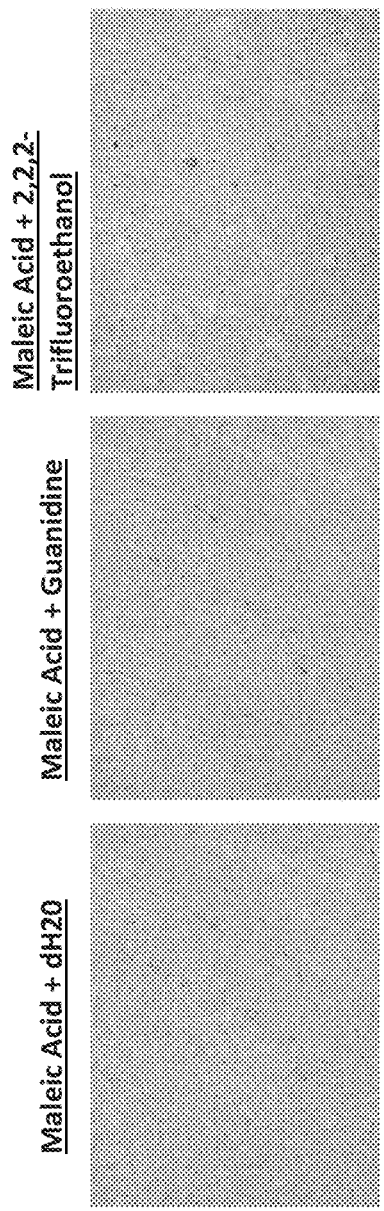
FIGS. 31A-31C shows microscope images of enhanced immunostaining of Collagen IV after antigen retrieval with maleic acid and cooling to room temperature in either guanidine (FIG. 31B) or 2,2,2-triflouroethanol (FIG. 31C) compared to dH$_2$O (FIG. 31A).

Antigen Retrieval (Adrenocorticotropic Hormone (ACTH)) by Formaldehyde Scavenging Agents ACTH (18-39) peptide is treated with formalin at room temperature for 48 hours (FIG. 12A). Then, 5% maleic acid (FIG. 12B), 5% ascorbic acid (FIG. 12C) and water at pH=3.5 (FIG. 12D) are used to treat the formalin treated ACTH peptide at 90° C. for 45 minutes respectively. The composition of the formalin treated ACTH after each treatment is analyzed using mass spectrometry. The results shown in FIGS. 12A-12D are used to investigate the ability of the agents to reverse formaldehyde adducts. FIG. 12A shows the composition of ACTH after formalin treatment, which results in high content of ACTH with 2 methylene units (m/z 2489) and ACTH with 1 methylene unit (m/z 2477). Only a small amount of ACTH with 3 methylene units is detected. Comparisons of FIGS. 12A, 12B, and 12C indicate that both 5% maleic acid and 5% ascorbic acid are able to convert almost all the modified ACTH (ACTH with 1, 2 or 3 methylene groups; m/z 2477, 2489 and 2501 respectively) into unmodified ACTH (m/z 2465) at 98° C. for 45 minutes.

Example 13

Preparation of Tissue Samples 12-month-old C57Bl6J mice were housed under controlled environment conditions on a condition al 12 hour light dark cycle. Following sacrifice, brains were post-fixed in 4% paraformaldehyde for 72 hours at 40° C. and then transferred to 70% ethanol solution where they were stored at 4° C. Tissue was paraffin-processed using convention dehydration and embedding, and then sectioned at 5 μm intervals.

Example 14

Standard Protocol for Antigen Retrieval

Tissues were deparaffinized and rehydrated. Slides were placed in a plastic Coplin jar containing either distilled water or a combination of formaldehyde scavengers in combination with an enhancer. Jars were covered with a loose fitting screw cap and heated in a pressure cooker for 45 minutes at 95° C. After heating, the Coplin jars were removed and allowed to cool and rinsed in TBST for five minutes.

Example 15

Immunohistochemistry

Immunohistochemical staining was performed using a three-step immunostaining technique using the ABC method. Briefly, all incubations were performed as follows: 1) primary antibodies were incubated overnight at 4° C., 2) secondary antibodies were incubated for 10 minutes at room temperature, 3) streptavidin-conjugated enzyme was incubated for 10 minutes at room temperature, 4) peroxidase substrate was incubated for 1 minute.

Example 16

Preparation of Tissues Samples 12-month-old C57Bl6J mice were housed under controlled environment conditions on a condition al 12 hour light dark cycle. Following sacrifice, brains were post-fixed in 4% paraformaldehyde for 72 hours at 4° C. and then transferred to 70% ethanol solution where they were stored at 4° C. Tissue was paraffin-processed using convention dehydration and embedding, and then sectioned at 5 μm intervals.

Example 17

Standard Protocol for Antigen Retrieval

Tissues were deparaffinized and rehydrated. Slides were placed in a plastic Coplin jar containing either distilled water or 0.05% Maleic Acid. Jars were covered with a loose fitting screw cap and heated in a pressure cooker for 45 minutes at 95° C. After heating, the Coplin jars were removed and slides were allowed to cool to room temperature in either 10% guanidine or 2,2,2-trifluoroethanol in water and rinsed in TBST for five minutes.

Example 18

Immunohistochemistry

Immunohistochemical staining was performed using a three-step immunostaining technique using the ABC method. Briefly, all incubations were performed as follows: 1) primary antibodies were incubated overnight at 4° C., 2) secondary antibodies were incubated for 10 minutes at room temperature, 3) streptavidin-conjugated enzyme was incubated for 10 minutes at room temperature, 4) peroxidase substrate was incubated for 1 minute.

TABLE 2

Immunohistochemical Staining of Collagen IV on Formalin Fixed Paraffin Embedded Mouse Brain Sections.

| Compound | Result |
| --- | --- |
| p-Anisidine | ++ |
| Aniline | ++ |
| Sulfanilic acid | ++ |
| 4-Aminophenol | ++ |
| 4-Ethoxyaniline | + |
| p-Phenylenediamine | + |
| 2-Amino-5-methoxybenzoic acid | − |

Immunoreactivity was scored on a scale of − to +++, − being non-reactive and +++ being highly reactive.

TABLE 3

Immunohistochemical Staining of Collagen IV on Formalin Fixed Paraffin Embedded Mouse Brain Sections.

| Compound | Result |
| --- | --- |
| 1% Hydroxylamine | + |
| 1% Hydroxylamine + 0.1% 4-Aminophenol | ++ |
| 1% Hydroxylamine + 0.5% 4-Aminophenol | +++ |

TABLE 4

Immunohistochemical Staining of Collagen IV on Formalin Fixed Paraffin Embedded Mouse Brain Sections.

| Compound | Result |
| --- | --- |
| 1% Hydroxylamine | + |
| 1% Hydroxylamine + 0.1% Aniline | ++ |
| 1% Hydroxylamine + 0.5% | +++ |

TABLE 5

Immunohistochemical Staining of Collagen IV on Formalin Fixed Paraffin Embedded Mouse Brain Sections.

| Compound | Result |
| --- | --- |
| 0.5% Hydroxylamine | + |
| 0.5% Hydroxylamine + 0.1% Aniline | ++ |
| 0.5% Hydroxylamine + 0.5% | ++ |

TABLE 6

Immunohistochemical Staining of Collagen IV on Formalin Fixed Paraffin Embedded Mouse Brain Sections.

| Compound | Result |
| --- | --- |
| 1% O-Benzylhydroxylamine | + |
| 1% O-Benzylhydroxylamine + 0.1% Aniline | ++ |
| 1% O-Benzylhydroxylamine + 0.5% | +++ |

TABLE 7

Immunohistochemical Staining of Collagen IV on Formalin Fixed Paraffin Embedded Mouse Brain Sections.

| Compound | Result |
| --- | --- |
| 0.5% O-Benzylhydroxylamine | + |
| 0.5% O-Benzylhydroxylamine + 0.1% Aniline | ++ |
| 0.5% O-Benzylhydroxylamine + 0.5% | +++ |

TABLE 8

Immunohistochemical Staining of Collagen IV on Formalin Fixed Paraffin Embedded Mouse Brain Sections.

| Compound | Result |
| --- | --- |
| 0.05% Maleic acid | + |
| 0.05% Maleic acid + 0.1% Aniline | ++ |
| 0.05% Maleic acid + 0.5% Aniline | ++ |

TABLE 9

Immunohistochemical Staining of Collagen IV on Formalin Fixed Paraffin Embedded Mouse Brain Sections.

| Compound | Result |
| --- | --- |
| dH20 | + |
| Guanidine | ++ |
| 2,2,2-Trifluoroethanol | ++ |

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for retrieving at least one molecular recognition element in a fixed tissue, comprising the steps of:
    preparing a solution comprising an aldehyde-scavenging agent; and
    contacting the fixed tissue with the solution;
    wherein the tissue is fixed with an aldehyde-based cross-linking agent, wherein a reaction of the aldehyde scavenging agent with the aldehydes comprising the cross-linking agent retrieves at least one molecular recognition element, wherein at least one molecular recognition element comprises amino acids, peptides, proteins, nucleic acids, carbohydrates, lipids, or a combination thereof, and wherein the aldehyde-scavenging agent comprises of at least one member selected from the group consisting of beta-dicarbonyl compounds, mono or di-amide scavengers, ethyl alcohols, sulfur containing compounds, mercaptoethylamines, hydrazines, ethanolamines, hydroxylamines, anilines, ammonium bicarbonate, pyridoxamine, or mixtures and combinations thereof.

2. The method of claim 1, wherein the aldehyde-based cross-linking agent is formaldehyde or glutaraldehyde.

3. The method of claim 1, wherein the concentration of the aldehyde-scavenging agent in the solution is about 0.01% to about 30%.

4. The method of claim 3, wherein the pH of the solution is within a range specific for the aldehyde scavenging agent or mixture of agents.

5. The method of claim 1, further comprising heating the solution from about 60° C. to about 125° C. to reach a reversible equilibrium between aldehyde and aldehyde adducts.

6. The method of claim 5, wherein the solution reduces auto-fluorescence in heated tissues.

7. The method of claim 5 further comprising:
cooling the solution to room temperature; and
contacting the tissue fixed with the aldehyde-based cross-linking agent with a second solution, wherein the second solution comprises of at least one chaotropic agent.

8. The method of claim 7, wherein the chaotropic agent is guanidine.

9. The method of claim 7, wherein the chaotropic agent is trifluroethanol.

10. The method of claim 1, further comprising the step of detecting at least one molecular recognition element.

11. The method of claim 10, wherein the step of detecting comprises staining the tissue to detect at least one molecular recognition element.

12. The method of claim 1, wherein the beta-dicarbonyl compounds comprise acetoacetamide, and 5,5-dimethyl-1,3-cylohexanedione (dimedone), methyl acetoacetate.

13. The method of claim 1, wherein the mono or di-amide scavengers comprise 2-pyrrolidinone, succinimide, barbituric acid, tannic acid, and L-asparagine.

14. The method of claim 1, wherein the ethyl alcohols comprise polyvinyl alcohol.

15. The method of claim 1, wherein the sulfur containing compounds comprise 1, 3, 5-triazine-2, 4, 6-trithiol, sodium bisulfite, and sodium metabisulfite.

16. The method of claim 1, wherein the mercaptoethylamines comprise cysteamine and cysteine.

17. The method of claim 1, wherein the hydrazines comprise Girard T reagent, and 2,4-dinitrophenylhydrazine.

18. The method of claim 1, wherein the ethanolamines comprise 2-amino-1-butanol and 2-amino-2-methyl-1,3-propanediol.

19. The method of claim 1, wherein the hydroxylamines comprise hydroxylamine, O-benzylhydroxylamine, O-carboxymethylhydroxylamine, O-ethylhydroxylamine, and O-phenylhydroxylamine.

20. The method of claim 1, wherein the anilines comprise p-anisidine, aniline, sulfanilic acid, 4-aminophenol, 4-ethoxyaniline, p-phenylenediamine, and 2-amino-5-methoxybenzoic acid.

21. The method of claim 1, wherein the solution comprises hydroxylamine and 4-aminophenol.

22. The method of claim 1, wherein the solution comprises hydroxylamine and aniline.

23. The method of claim 1, wherein the solution comprises O-benzylhydroxylamine acid and aniline.

24. The method of claim 1, wherein the solution further comprises about 0.1% to about 5% of a nonionic surfactant.

25. The method of claim 24, wherein the nonionic surfactant is effective in removing paraffin from a paraffin-embedded sample to enhance fluorescence intensity of the detected epitope.

26. The method of claim 24, wherein the nonionic surfactant is polyethylene glycol monohexadecyl ether, cetostearyl alcohol, cetyl alcohol, cocamide diethanolamine, cocamide monoethanolamine, decyl glucoside, octylphenoxypolyethoxyethanol, polyethylene glycol monoisohexadecyl ether, lauryl glucoside, nonyl phenoxypolyethoxylethanol, 4-Nonylphenyl-polyethylene glycol, 1-(4-Nonylphenyl)-1,4,7,10,13,16,19,22,25-nonaoxaheptacosan-27-ol, nonoxynols, monolaurin, octaethylene glycol monododecyl ether, oleyl alcohol, polyethylene-polypropylene glycol, polyglycerol polyricinoleate, polysorbates, sorbitan monostearate, sorbitan tristearate; stearyl alcohol; polyethylene glycol p-(1,1,3,3-tetramethylbutyl)-phenyl ether; polyoxyethylene (20) sorbitan monooleate, octyl-, decyl, dodecyl-glucopyranoside, -maltoside or deoxycholic acid.

27. The method of claim 1, wherein the solution further contains a stabilizing agent selected from a preservative, an antifungal agent, an antibacterial agent, a dye, a pigment, anionic detergents, metal salts, antioxidants or a combination thereof.

* * * * *